US007368100B2

(12) United States Patent
Brechbiel et al.

(10) Patent No.: US 7,368,100 B2
(45) Date of Patent: May 6, 2008

(54) BACKBONE-SUBSTITUTED BIFUNCTIONAL DOTA LIGANDS, COMPLEXES AND COMPOSITIONS THEREOF, AND METHODS OF USING SAME

(75) Inventors: Martin W. Brechbiel, Annadale, VA (US); Hyun-Soon Chong, Chicago, IL (US)

(73) Assignee: The United States of America, represented by the Secretary, Department of Health and Human Services, Washington, DC (US)

( * ) Notice: Subject to any disclaimer, the term of this patent is extended or adjusted under 35 U.S.C. 154(b) by 353 days.

(21) Appl. No.: 10/525,673

(22) PCT Filed: Sep. 5, 2003

(86) PCT No.: PCT/US03/27878

§ 371 (c)(1),
(2), (4) Date: Apr. 18, 2005

(87) PCT Pub. No.: WO2004/021996

PCT Pub. Date: Mar. 18, 2004

(65) Prior Publication Data

US 2006/0165600 A1   Jul. 27, 2006

Related U.S. Application Data

(60) Provisional application No. 60/408,676, filed on Sep. 6, 2002.

(51) Int. Cl.
*A61B 5/055*   (2006.01)
*C07F 5/00*   (2006.01)
*C07D 225/00*   (2006.01)
*C07D 255/02*   (2006.01)
*C07D 257/02*   (2006.01)
*C07D 259/00*   (2006.01)
*C07D 245/00*   (2006.01)
*C07D 487/00*   (2006.01)

(52) U.S. Cl. ............. 424/9.363; 534/16; 540/465; 540/474; 540/473

(58) Field of Classification Search ............. 424/9.363
See application file for complete search history.

(56) References Cited

U.S. PATENT DOCUMENTS

| 4,923,985 | A | | 5/1990 | Gansow et al. | |
|---|---|---|---|---|---|
| 5,049,667 | A | * | 9/1991 | Schaefer et al. | 540/474 |
| 5,334,371 | A | | 8/1994 | Gries et al. | |
| 5,358,704 | A | * | 10/1994 | Desreux et al. | 424/9.363 |
| 5,428,154 | A | * | 6/1995 | Gansow et al. | 540/465 |
| 5,428,156 | A | * | 6/1995 | Mease et al. | 540/474 |
| 5,434,287 | A | | 7/1995 | Gansow et al. | |

FOREIGN PATENT DOCUMENTS

| WO | WO 89/11475 A1 | 11/1989 |
|---|---|---|
| WO | WO 95/19347 A1 | 7/1995 |
| WO | WO 95/31444 A1 | 11/1995 |
| WO | WO 96/14339 A1 | 5/1996 |
| WO | WO 02/062398 A2 | 8/2002 |
| WO | WO 03/101919 A2 | 12/2003 |

OTHER PUBLICATIONS

Moi et. al.; 1988; J. Am. Chem. Soc. 110, 6266-6267.*
Benter, Yinon; Gadolinium; www.chemicalelements.com/elements/gd.html.*
Atsarkin et al., *J. Phys. Chem. A.*, 105(41), 9323-9327 (2001).
Cox et al., *J. Chem. Soc. Perkin Trans.*, 1, 2567-2576 (1990).
Forsberg et al., *Inorg. Chem.*, 34(14), 3705-3715 (1995).
Hnatowich et al., *Science*, 220, 613-615 (1983).
Howard et al., *Chem. Commun.*, 1381-1382 (1998).
Jacques et al., *J. Alloys Compd.*, 249, 173-177 (1997).
Kasprzyk et al., *Inorg. Chem.*, 21(9), 3349-3352 (1982).
Keire et al., *Inorg. Chem.*, 40(17), 4310-4318 (2001).
Kline et al., *Bioconjugate Chem.*, 2(1), 26-31 (1991).
Kodama et al., *Inorg. Chem.*, 30(6), 1270-1273 (1991).
Krejcarek et al., *Biochem. Biophys. Res. Commun.*, 77(2), 581-585 (1977).
Lewis et al., *Bioconjugate Chem.*, 5(6), 565-576 (1994).
Lewis et al., *Bioconjugate Chem.*, 12(2), 320-324 (2001).
McCall et al., *Bioconjugate Chem.*, 1(3), 222-226 (1990).
McMurray et al., *Bioconjugate Chem.*, 3(2), 108-117 (1992).
Milenic et al., *Nuclear Medicine and Biology*, 29, 431-442 (2002).
Mirzadeh et al., *Bioconjugate Chem.*, 1(1), 59-65 (1990).
Peterson et al., *Bioconjugate Chem.*, 10(2), 316-320 (1999).
Ruegg et al., *Cancer Res.*, 50, 4221-4226 (1990).
Runge et al., *Invest. Radiol.*, 30(2), 123-130 (1995).
Siaugue et al, *Tetrahedron Letters*, 41, 7443-7446 (2000).
Szilágyi et al., *Inorg. Chim. Acta.*, 298, 226-234 (2000).
Takenouchi et al., *J. Org. Chem.*, 58, 6895-6899 (1993).
Wu et al., *Bioorg. Med. Chem.*, 5(10), 1925-1934 (1997).
Bambirra et al., *Chem. Commun.*, 637-638 (2001).
Berreau et al., *Inorg. Chem.*, 37, 1091-1098 (1998).
Chong et al., *J. Med. Chem.*, 45(16), 3458-3464 (2002).
Curtis et al., *J. Chem. Soc. A.*, 1015-1018 (1966).
Fortier et al., *J. Chem. Soc. Dalton Trans.*, 101-109 (1991).
Kovacs et al., *Synth. Commun.*, 29(16), 2817-2822 (1999).
Male et al., *Inorg. Chem.*, 39, 5483-5491 (2000).

(Continued)

*Primary Examiner*—Jeffrey H Murray
(74) *Attorney, Agent, or Firm*—Leydig, Voit & Mayer, Ltd.

(57) ABSTRACT

Backbone-substituted 1,4,7,10-tetraaza cyclododecane-N, N',N'',N'''-tetraacetic acid compounds, metal complexes thereof, compositions thereof, conjugates thereof, and methods of use in diagnostic imaging and treatment of a cellular disorder.

22 Claims, 6 Drawing Sheets

OTHER PUBLICATIONS

Pletnev, *Can. J. Chem.*, 72, 1404-1411 (1994).
Renn et al., *Bioconjugate Chem.*, 3, 563-569 (1992).
Rossi et al., *Tetrahedron Letters*, 39, 7159-7162 (1998).
Tei et al., *J. Chem. Soc. Dalton Trans.*, 2793-2799 (2000).
Warden et al., *Org. Lett.*, 3(18), 2855-2858 (2001).
Weisman et al., *J. Org. Chem.*, 61, 5186-5187 (1996).
Chappell et al., *Nuclear Medicine and Biology*, 30, 581-595 (2003).

* cited by examiner

BACKBONE-SUBSTITUTED BIFUNCTIONAL DOTA LIGANDS, COMPLEXES AND COMPOSITIONS THEREOF, AND METHODS OF USING SAME

FIELD OF THE INVENTION

This invention pertains to backbone-substituted macrocyclic chelates, metal complexes thereof, and methods of using same.

BACKGROUND OF THE INVENTION

Monoclonal antibodies (mAbs) have been employed as targeting biomolecules for the delivery of radionuclides into tumor cells in radioimmunotherapy (RIT). Numerous clinical trials have been performed to validate this modality of cancer therapy (see, for example, Parker et al., *Pure Appl. Chem.*, 63, 427-463 (1991); Chakrabarti et al., *J. Nuc. Med.*, 3.7, 1384-1388 (1996); Sharkey et al., *Cancer Res.*, 48, 3270-3275 (1988); Sharkey et al., *Cancer Res.*, 48, 3270-3275 (1988); and Lee et al., *Cancer Res.*, 50, 4546-4551 (1990)). Several useful $\beta^-$-emitting radionuclides, including $^{131}$I, $^{90}$Y, $^{177}$Lu, $^{153}$Sm, $^{213}$Bi, $^{212}$Bi, $^{212}$Pb and $^{225}$Ac, have been employed for labeling mAbs for RIT applications (Denardo et al., *Cancer*, 73, 1012-1022 (1994); Scott et al., *Cancer*, 73, 993-998 (1994); Schlom et al., *Cancer Res.*, 51, 2889-96 (1991)).

While one critical variable that influences the effectiveness of RIT is the choice of the radionuclide and its associated emission characteristics, an equally important aspect is the choice of the chemical means by which the radionuclide is bound to the protein. For RIT applications, $^{90}$Y or $^{177}$Lu must be linked as the metal complex to a monoclonal antibody (mAb) or immunoprotein via a suitable bifunctional chelating agent, wherein that complex must be adequately thermodynamically and kinetically stable to minimize release of the isotope in order to minimize toxicity in vivo (Gansow et al., *Nucl. Med Biol.*, 18, 369-381 (1991)).

The pure $\beta^-$-emitting radionuclide $^{90}$Y ($E_{max}$=2.28 MeV; $t_{1/2}$=64.1 h) has been extensively studied in RIT due to its physical properties (see, for example, Martell et al., *Critical Stability Constants*, Vol. 1: Amino Acids. Plenum Press: New York, 1974; pp. 281-284; Wessels et al., *Med Phys.*, 11, 638-645 (1984); Chinol et al., *J. Nucl. Med.*, 28, 1465-1470 (1987); and Mausner et al., *Med Phys.*, 20, 503-509 (1993)). The macrocyclic chelating agent 1,4,7,10-tetraazacyclododecane-N,N',N",N"'-tetraacetic acid ("DOTA")

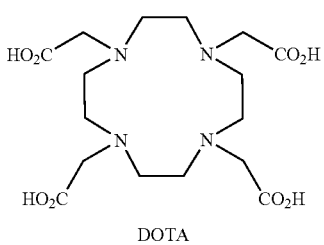

DOTA is well-known to be an effective chelator of Y(III) and lanthanides. Numerous bifunctional analogs of DOTA suitable for protein conjugation have been reported in the literature (Szilágyi et al., *Inorg. Chim. Acta*, 298, 226-234 (2000); Kodama et al., *Inorg. Chem.*, 30, 1270-1273 (1991); Kasprzyk et al., *Inorg Chem.*, 21, 3349-3352 (1982); Cox et al., *J. Chem. Soc. Perkin Trans.* 1, 2567-2576 (1990); Kline et al., *Bioconjugate Chem.*, 2, 26-31 (1991); and McCall et al., *Bioconjugate Chem.*, 1, 222-226 (1991)).

However, the formation kinetics associated with the DOTA chelating agent also has been found to be less than optimal, requiring either lengthy radiolabeling protocols and/or the use of elevated temperatures to achieve acceptable yields and specific activities. (Ruegg et al., *Cancer Res.*, 50, 4221-4226 (1990); Lewis et al., *Bioconjugate Chem.* 5, 565-576 (1994)) Alternate approaches for using DOTA have resulted in the development of numerous derivatives wherein modifications of the DOTA framework have been explored to address this deficiency. This has been pursued by either the addition of external chelating moieties (Takenouchi et al., *J. Org. Chem.*, 58, 6895-6899 (1993)), conversion of one of the carboxylates to an amide for conjugation purposes (Lewis et al., *Bioconjugate Chem.*, 5, 565-576 (1994); Lewis et al., *Bioconjugate Chem.*, 12, 320-324 (2001); and Peterson et al., *Bioconjugate Chem.*, 10, 316-320 (1999)), or altering the carbon chain length of the carboxylate (Keire et al., *Inorg. Chem.*, 40, 4310-4318 (2001)). While all of these investigations have met with varying levels of success with actual use, resolution of inherently slow formation kinetics and radiolabeling inefficiency remains.

For example, several bifunctional derivatives of DOTA have been synthesized for radiolabeling proteins, including 2-(p-isothiocyanatobenzyl)-1,4,7,10-tetraazacyclododecane-1,4,7,10-tetraacetic acid (C-DOTA), and 1,4,7,10-tetraaza-N-(1-carboxy-3-(4-nitrophenyl)propyl)-N',N",N"'-tris (acetic acid) cyclododecane (PA-DOTA)

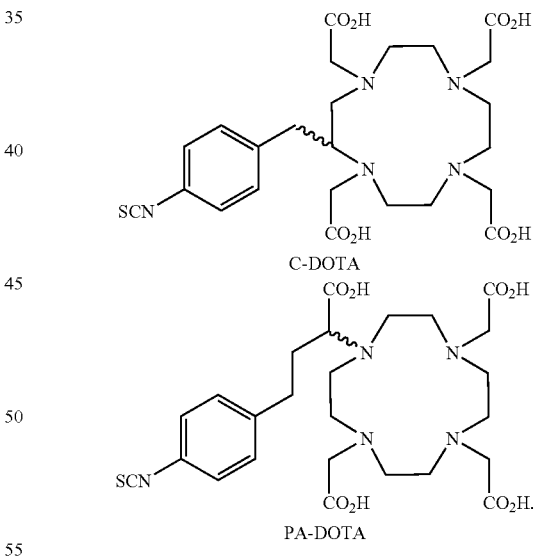

C-DOTA

PA-DOTA

One aspect that all of these previously reported derivatives have in common is that the tetraaza ring was retained without any modification. There have been numerous detailed studies of the mechanism of metal ion complex formation with DOTA, as well as with amido and phosphorus analogues (Forsberg et al., *Inorg. Chem.*, 34, 3705-3715 (1995); and Howard et al., *Chem. Commun.*, 1381-1382 (1998)). These studies generally propose a two-step mechanism of electrostatic capture of the metal, followed by encapsulation, during which there is deprotonation of the amines and an associated energy cost due to arrangement of the carboxylates in the proper geometries for metal binding (Howard et al. (1998), supra). One aspect of this process also includes arranging the 12-membered ring into the proper spatial geometry, a process that also has an associated energy cost. The final geometry of the lanthanide DOTA complexes has been well reported (Forsberg et al., (1995), supra; and Howard et al. (1998), supra). Forsberg and co-workers have reported on the preferential ring geometry of these complexes via modeling the tetra-amido DOTA complexes (Forsberg et al., (1995), supra).

The value of having a ligand conjugate to chelate metal ions for therapeutic, diagnostic, or other uses is of commercial importance. This commercial importance is due to the fact that many metal ions have desirable characteristics for these various uses, but the delivery systems for the metal ions lack specificity to target cells or do not adequately bind the metal ions.

Therefore, there is still a need for compounds that possess complex stability comparable to that of DOTA and increased stability in vitro and in vivo. The invention provides such compounds, complexes and compositions thereof and methods related thereto. These and other objects and advantages, as well as additional inventive features, will be apparent from the description of the invention provided herein.

BRIEF SUMMARY OF THE INVENTION

The present invention provides a compound of the formula (I)

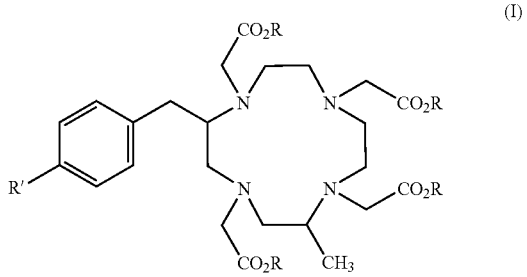

(I)

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido.

The present invention also provides a compound of the formula (II)

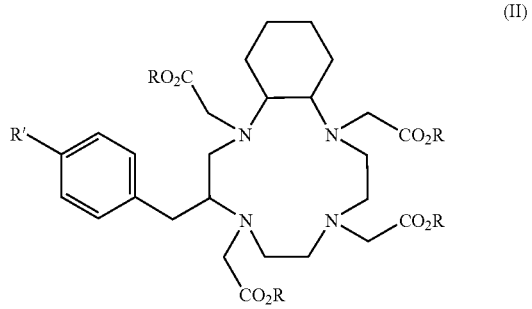

(II)

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido Further provided is a compound of the formula (III)

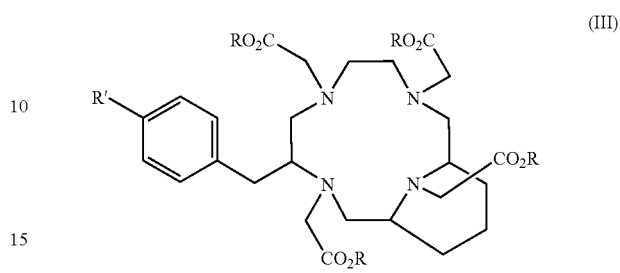

(III)

wherein R is hydrogen or alkyl and R' is selected from the group consisting hydrogen, halo, alkyl, hydroxy, nitro, amino, alkylamino, thiocyano, isothiocyano, carboxyl, carboxyalkyl, carboxyalkyloxy, amido, alkylamido and haloalkylamido.

Still further provided is a complex comprising the compound of formula (I), (II) or (III) and a metal ion.

A pharmaceutical composition comprising a pharmaceutically acceptable carrier and a compound of formula (I), (II), or (III), or a metal complex thereof is also provided.

A method for diagnostic imaging of a host is further provided. The method comprises administering to the host a complex of formula (I), (II), or (III), in an amount effective to provide an image; and exposing the host to an energy source, whereupon a diagnostic image of the host is obtained.

Still further provided is a method for treating a cellular disorder in a mammal. The method comprises administering to the mammal a complex of formula (I), (II), or (III) in an amount effective to treat the cellular disorder, whereupon the cellular disorder in the mammal is treated.

DETAILED DESCRIPTION OF THE INVENTION

Figure 1:
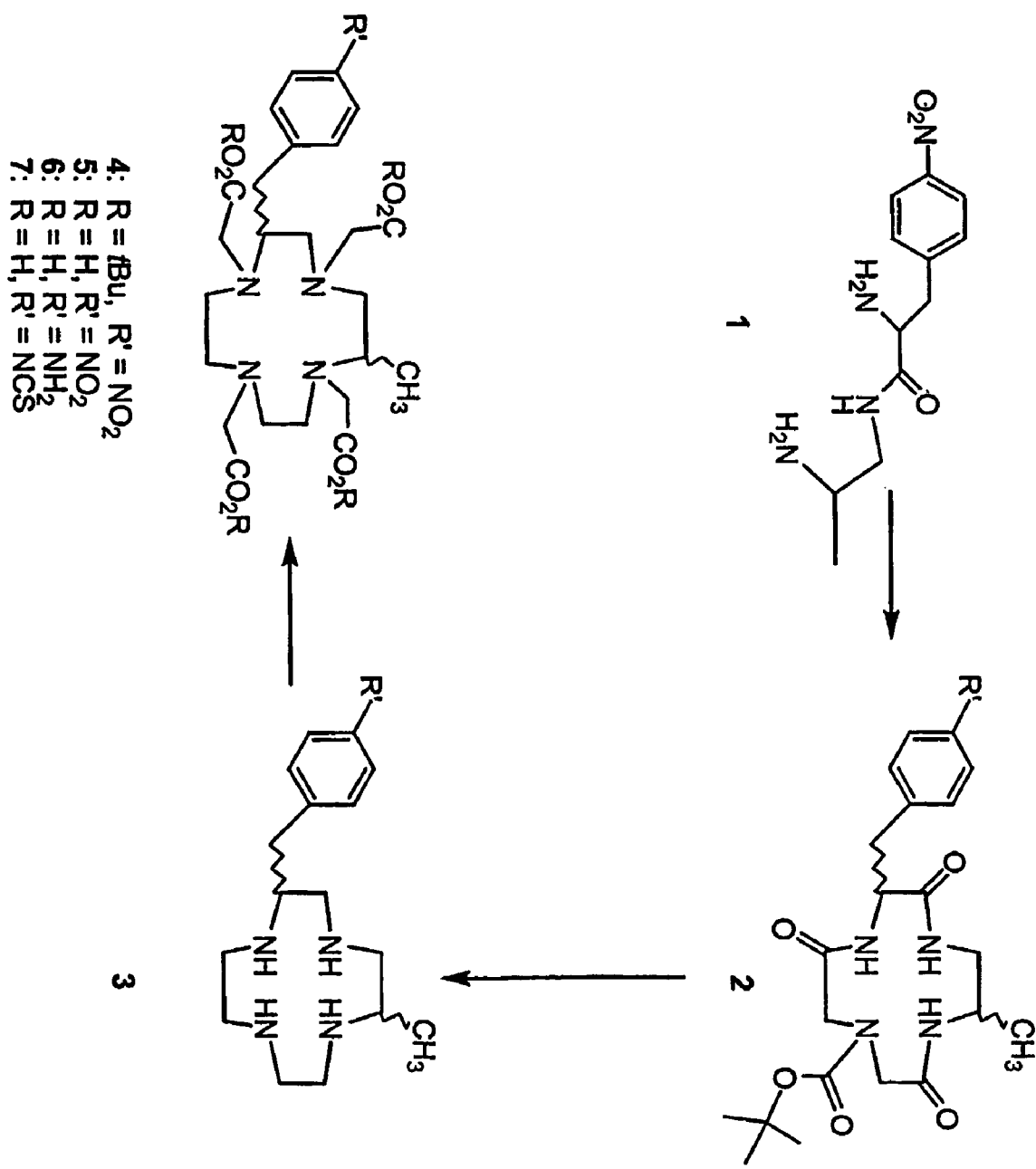
FIG. 1 illustrates the chemical synthesis of 2-methyl-6-p-substituted-benzyl)-1,4,7,10-tetraazacyclododecane-1,4,7,10-tetraacetate (Formula I).

The invention provides backbone-substituted 1,4,7,10-tetraaza cyclododecane-N,N',N'',N'''-tetraacetic acid, (i.e., DOTA compounds). The DOTA derivatives of the invention are such that the macrocyclic backbone was pre-arranged or pre-organized in order to lower the energy barrier to complex formation, thereby potentially increasing the rate of complex formation. The pre-organization and macrocyclic effect of the DOTA sub-structure accelerates complexation with metal ions and isotopes (e.g., Y(III), Gd(III); etc.), while maintaining a high level of stability of the complexes.

More specifically, the present invention provides a compound of the formula (I)

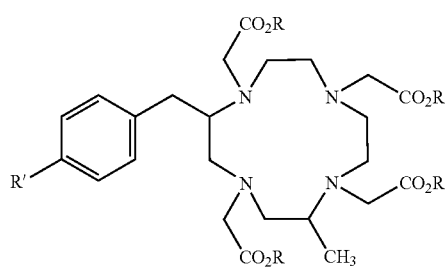

(I)

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido.

The present invention also provides a compound of the formula (II)

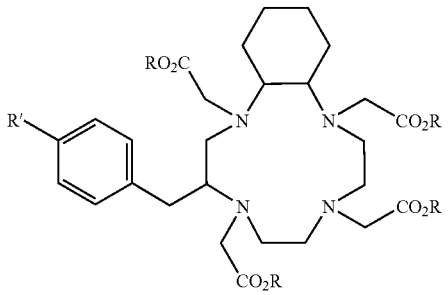

(II)

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido.

Preferably, the compound of the formula (II) is

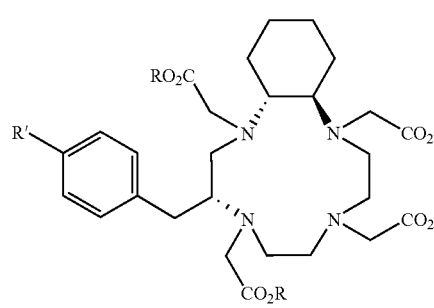

(II)

The invention also provides a compound of the formula (III)

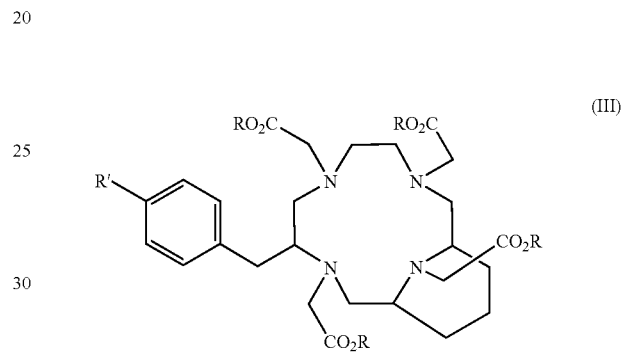

(III)

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido.

Preferably, the compound of the formula (III) is

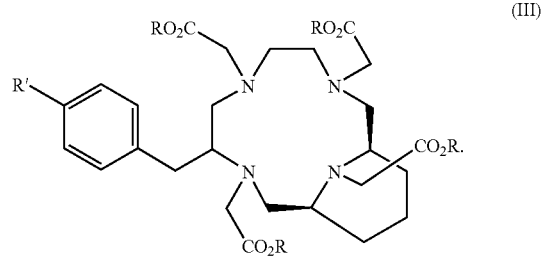

(III)

The term "halo" or "halogen," as used herein, means a substituent selected from Group VIIA of the Periodic Table of Elements, such as, for example, fluorine, bromine, chlorine, and iodine. Preferably, the halo is bromo or iodo.

The term "alkyl" means a straight-chain or branched alkyl substituent containing from, for example, 1 to about 12 carbon atoms, preferably from 1 to about 8 carbon atoms, more preferably from 1 to about 6 carbon atoms. Examples of such substituents include methyl, ethyl, propyl, isopropyl, n-butyl, sec-butyl, isobutyl, tert-butyl, pentyl, isoamyl, hexyl, octyl, dodecanyl, and the like.

The term "cycloalkyl," as used herein, means a cyclic alkyl substituent containing from, for example, about 3 to about 30 carbon atoms, preferably from about 5 to about 14 carbon atoms, more preferably from about 5 to about 10 carbon atoms, and most preferably from about 5 to about 7 carbon atoms. The term includes both monocyclic and polycyclic (e.g., bicyclic) structures. Examples of such substituents include cyclopropyl, cyclobutyl, cyclopentyl, cyclohexyl, and the like.

The term "alkylamino" refers to a secondary amine substituent with one hydrogen and one alkyl group directly attached to a trivalent nitrogen atom. In addition, the term "alkylamino" also refers to a tertiary amine substituent with two of the same or different alkyl groups directly attached to a trivalent nitrogen atom. The alkyl group is described above.

The term "carboxyl" refers to the group —C(O)OH. The term "carboxyalkyl" refers to the group —R"C(O)OH that is connected to the compound through the alkyl R" group. The term "carboxyalkyloxy" refers to the group —OR"C(O)OH, in which the R" is an alkyl (e.g., $(CH_2)_n$ alkylene group, n is 1 to 12) group. The alkyl group is described above.

The term "alkylamido" refers to substituents of the formula, —C(O)NR'R" or —NR'C(O)R", in which R' and R" are the same or different and each is a hydrogen or alkyl group, as described above. The term "haloalkylamido" is an alkylamido, in which one or more of the alkyl groups is substituted with a halo moiety as described above, such as, for example, chloro, bromo or iodo.

The term "aryl" refers to an unsubstituted or substituted aromatic carbocyclic substituent, as commonly understood in the art, and includes monocyclic and polycyclic aromatics such as, for example, phenyl, biphenyl, toluenyl, anisolyl, naphthyl, anthracenyl and the like. An aryl substituent generally contains from, for example, about 3 to about 30 carbon atoms, preferably from about 6 to about 18 carbon atoms, more preferably from about 6 to about 14 carbon atoms and most preferably from about 6 to about 10 carbon atoms. It is understood that the term aryl applies to cyclic substituents that are planar and comprise $4n+2\pi$ electrons, according to Hückel's Rule.

The term "heteroaryl" means a substituent defined by an aromatic heterocyclic ring, as is commonly understood in the art, including monocyclic and polycyclic heteroaryls containing from, for example, about 3 to about 30 carbon atoms, preferably from about 5 to about 10 carbon atoms, more preferably from about 5 to about 6 carbon atoms. Monocyclic heteroaryls include, for example, imidazolyl, thiazolyl, pyrazolyl, pyrrolyl, furanyl, pyrazolinyl, thiophenyl, oxazolyl, isoxazolyl, pyridinyl, pyridonyl, pyrimidinyl, pyrazinyl, and triazinyl substituents. Polycyclic heteroaryls include, for example, quinolinyl, isoquinolinyl, indolyl, purinyl, benzimidazolyl, benzopyrrolyl, and benzothiazolyl.

The term "alkoxy" embraces linear or branched alkyl groups that are attached to divalent oxygen. The alkyl group is the same as described herein. Examples of such substituents include methoxy, ethoxy, t-butoxy, and the like. The term "aryloxy" refers to substituents that have an aryl group attached to divalent oxygen. The aryl group is the same as described herein. Examples of such substituents include phenoxy.

The term "alkylthio" as used herein, denotes a substituent with an alkyl group directly attached to a divalent sulfur atom. The alkyl group is the same as described herein. Examples of such substituents include methylthio, ethylthio, and the like. Similarly, the term "arylthio" as used herein, denotes a substituent with an aryl group directly attached to a divalent sulfur atom. The aryl group is the same as described herein.

Any of the groups indicated above for R and R' for compounds of formula (I), (II) or (III) can optionally be substituted with 1 to 6 (e.g., 1 to 4, 1 to 3) substituents. Suitable substituents include hydroxy, $C_{1-12}$ alkoxy, acyloxy, halo, benzyl, acetyl, carboxyl, carboxy-$C_{1-12}$ alkyl, such as carboxymethyl or carboxyethyl, carboxy-$C_{1-12}$ alkylamido, carboxy-$C_{1-12}$ dialkylamido, carboxamido, amino, $C_{1-12}$ alkylamino, $C_{1-12}$ dialkylamino, $C_{1-12}$ alkylcarbonyl, $C_{6-30}$ arylamino, $C_{6-30}$ diarylamino, cyano, tolyl, xylyl, mesityl, anisyl, pyrrolidinyl, formyl, thio, $C_{1-12}$ alkylthio, $C_{6-30}$ aryl, $C_{5-30}$ heteroaryl, such as pyranyl, pyrrolyl, furanyl, thiophenyl, thiazolyl, pyrazolyl, pyridinyl, or pyrimidinyl, phenoxy, benzyloxy, phenylcarbonyl, benzylcarbonyl, nitrophenyl, $C_{1-12}$ trialkylsilyl, nitro, sulfonyl, nitrobenzyl, $C_{1-12}$ trialkylammonium, $C_{1-12}$ alkyl, $C_{3-8}$ cycloalkyl, such as cyclopropyl, cyclobutyl, cyclopentyl, or cyclohexyl, tetrahydrofuranyl, tetrahydropyranyl, piperidinyl and morpholinyl.

While any method can be used to prepare compounds of formula (I), (II) or (III), the synthetic methods provided herein are preferred. In general, the syntheses of compounds of formula (I), (II) or (III) are initiated from derivatives of p-substituted-phenylalanine. For example, synthesis of a compound of formula (I) begins with the cyclization reaction between amide 1 (FIG. 1), available from direct aminolysis with 1,2-diaminopropane of methyl p-nitrophenylalanine. This "1,7" diamine is reacted with the bis (succinimidyl) ester of BOC-iminodiacetic acid under relatively high-dilution conditions with equimolar addition controlled by addition of the two components via syringe pump. The product is isolated as a precipitate. This strategy can be directly applied to construct a wide range of macrocyclic rings by using functionalized amines (e.g., alkyl substituted, aryl substituted, heteroaryl substituted, cycloalkyl substituted; etc.). In brief, the requisite substituted diamines and subsequent substituted phenylalanines are readily available from extensive literature and the host of possibilities associated with amino acids to provide not only desired substituents and the appropriate regiochemistry, but also to provide them in desirable stereochemistry. This is equally the case for the other cyclization component. Additionally, the stereoselective introduction of substituents on the carboxylate functional groups is also readily available from routine, well-established amino acid chemistry.

The functionality of the R' substituent of the compounds of the invention allows conjugation to biomolecules to form conjugates. Accordingly, the present invention provides a conjugate comprising a compound of complex of formula (I), (II) or (III) and a biomolecule. The term "biomolecule" refers to all natural and synthetic molecules that play a role in biological systems. A biomolecule includes a hormone, an amino acid, a peptide, a peptidomimetic, a protein, deoxyribonucleic acid (DNA), ribonucleic acid (RNA), a lipid, an albumin, a polyclonal antibody, a receptor molecule, a receptor binding molecule, a hapten, a monoclonal antibody and an aptamer. Specific examples of biomolecules include insulins, prostaglandins, growth factors, liposomes and nucleic acid probes. An advantage of using biomolecules is tissue targeting through specificity of delivery.

Any suitable hapten can be linked with a compound or complex of formula (I), (II) or (III). Haptens such as hormones, steroids, enzymes and proteins are desirable in some applications because of their site specificity to tumors and/or various organs of the body. A preferred hapten for use in treating cellular disorders or various disease conditions is a monoclonal antibody. Methods of bonding a macrocyclic compound to a hapten are described in U.S. Pat. No. 5,428,154, which are incorporated herein by reference.

Coupling of a compound or complex of formula (I), (II) or (III) to one or more biomolecules can be accomplished by several known methods (see, for example, Krejcarek et al., *Biochem. Biophys. Res. Commun.*, 30, 581 (1977); and Hnatowich et al., *Science*, 220, 613 (1983)). For example, a reactive moiety present in the R' substituent is coupled with a second reactive group located on the biomolecule. Typically, a nucleophilic group is reacted with an electrophilic group to form a covalent bond between the biomolecule and the compound of formula (I), (II) or (III). Examples of nucleophilic groups include amines, anilines, alcohols, phenols, thiols and hydrazines. Examples of electrophilic groups include halides, disulfides, epoxides, maleimides, acid chlorides, anhydrides, mixed anhydrides, activated esters, imidates, isocyanates and isothiocyanates.

Preferably, the R' substituent of formula (I), (II) or (III) is a substituent that conjugates the compound to a hapten. This substituent is desirably a free-end nitro group, which can be reduced to an amine. The amine then can be activated with a compound, such as thionyl chloride, to form a reactive chemical group, such as an isothiocyanate. An isothiocyanate is preferred because it links directly to an amino residue of a hapten, such as an mAb. The aniline group can be linked to an oxidized carbohydrate on the protein and, subsequently, the linkage fixed by reduction with cyanoborohydride. The amino group also can be reacted with bromoacetyl chloride or iodoacetyl chloride to form —NHCOCH$_2$Z, with Z being bromide or iodide. This group reacts with any available amine or sulfhydryl group on a hapten to form a stable covalent bond. The most desirable R' substituents for compounds of formula (I), (II) or (III) are members selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido. In some preferred instances, R' is a haloalkylamido of the formula —NHCOCH$_2$Z, with Z being bromide or iodide. Another preferred substituent for this position is isothiocyano (—NCS).

The invention also relates to a complex comprising the compound of formula (I), (II) or (III) and a metal ion, in which is the metal ion is optionally radioactive. The metal ion is any metal ion that is suitable for the desired end use of the complex. For example, in proton magnetic resonance imaging, paramagnetic metal atoms such as gadolinium(I), manganese(II), manganese(II), chromium(E), iron(II), iron (III), cobalt(II), nickel(II), copper(I), praseodymium(II), neodymium(III), samarium(III), ytterbium(II), terbium(III), dysprosium(III), holmium(III), and erbium(III) (all are paramagnetic metal atoms with favorable electronic properties) are preferred as metals complexed by the ligands of formula (I), (II) or (III). Gadolinium(III) is the most preferred complexed metal due to the fact that it has the highest paramagnetism, low toxicity when complexed to a suitable ligand, and high lability of coordinated water. Typical metal ions for forming a complex of the invention include Ac, Bi, Pb, Y, Mn, Cr, Fe, Co, Ni, Tc, In, Ga, Cu, Re, a lanthanide (i.e., any element with atomic number 57 to 71 inclusive) and an actinide (i.e., any element with atomic number 89 to 103 inclusive). For use as x-ray contrast agents, the metal ion must be able to absorb adequate amounts of x-rays (i.e., radio-opaque), such as, for example, indium, yttrium, lead, bismuth, gadolinium, dysprosium, holmium and praseodymium.

Compounds of formula (I), (II) or (III) also can be complexed with a radioactive metal ion for use as therapeutic agents (e.g., radiopharmaceuticals). Radioisotopes of any suitable metal ion are acceptable for forming metal complexes of the invention. For example, typical radioisotopes include technetium, bismuth, lead, actinium, carbon, nitrogen, iodine, fluorine, oxygen, tellurium, helium, indium, gallium, copper, rhenium, yttrium, samarium and holmium. Of these radioisotopes, yttrium is preferred. Specific examples of radionuclides suitable for complexing to a compound of formula (I), (II) or (III) for various imaging techniques, including single photon emission computed spectroscopy, are, for example, $^{213}$Bi, $^{212}$Bi, $^{212}$Pb $^{225}$Ac, $^{177}$Lu, $^{99m}$Tc, $^{111}$In, $^{11}$C, $^{13}$N, $^{123}$I, $^{186}$Re, $^{18}$F, $^{15}$O, $^{201}$Tl, $^{3}$He, $^{166}$Ho and $^{67}$Ga.

To prepare metal complexes of the invention, compounds of formula (I), (II) or (III) are complexed with an appropriate metal or metal ion. This can be accomplished by any methodology known in the art. For example, the metal can be added to water in the form of an oxide, halide, nitrate or acetate (e.g., yttrium acetate, bismuth iodide) and treated with an equimolar amount of a compound of formula (I), (II) or (III). The compound can be added as an aqueous solution or suspension. Dilute acid or base can be added (where appropriate) to maintain a suitable pH. Heating at temperatures as high as 100° C. for periods of up to 24 hours or more can be employed to facilitate complexation, depending on the metal, the compound, and their concentrations.

Pharmaceutically acceptable salts of the metal complexes of the compounds of formula (I), (II) or (III) are also useful as imaging agents. These salts can be prepared by using a base (e.g., an alkali metal hydroxide, meglumine, arginine or lysine) to neutralize the above-prepared metal complexes, while they are still in solution. Some of the metal complexes are formally uncharged and do not need cations as counterions. Such neutral complexes may be preferred as intravenously administered x-ray and NMR imaging agents over charged complexes because they may provide solutions of greater physiologic tolerance due to their lower osmolality. However, for use as hepatobiliary agents, negatively charged ligands are preferred.

The invention further provides a pharmaceutical composition comprising a pharmaceutically acceptable carrier and a compound of formula (I), (II), (II), or a metal complex thereof. Pharmaceutically acceptable carriers, for example, vehicles, adjuvants, excipients, and diluents, are well-known to those ordinarily skilled in the art and are readily available to the public. The choice of carrier will be determined, in part, by the particular composition and by the particular method used to administer the composition. Accordingly, there is a wide variety of suitable formulations of the pharmaceutical compositions of the present invention.

One skilled in the art will appreciate that suitable methods of administering a composition of the present invention to an animal, e.g., a mammal such as a human, are also known. Although more than one route can be used to administer a particular composition, a particular route can provide a more immediate and more effective result than another route.

Formulations suitable for oral administration can consist of (a) liquid solutions, such as an effective amount of the compound of formula (I), (II) or (III) dissolved in a diluent, such as water or saline, (b) capsules, sachets or tablets, each containing a predetermined amount of the active ingredient, as solids or granules, (c) suspensions in an appropriate liquid, and (d) suitable emulsions.

Tablet forms can include one or more of lactose, mannitol, cornstarch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The compounds of formula (I), (II) or (III), alone or in combination with other suitable components, can be made into aerosol formulations to be administered via inhalation. These aerosol formulations can be placed into pressurized acceptable propellants, such as dichlorodifluoromethane, hydrofluorocarbon (such as HFC 134a and/or 227), propane, nitrogen, and the like.

Formulations suitable for parenteral administration include aqueous and non-aqueous solutions, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame or an amount sufficient to allow for diagnostic imaging of the desired tissue or organ. The dose will be determined by the strength of the particular compositions employed and the condition of the animal (e.g., human), as well as the body weight of the animal (e.g., human) to be treated. The size of the dose also will be determined by the existence, nature, and extent of any adverse side effects that might accompany the administration of a particular composition. A suitable dosage for internal administration is 0.01 to 100 mg/kg of body weight per day, such as 0.01 to 35 mg/kg of body weight per day or 0.05 to 5 mg/kg of body weight per day. A suitable concentration of the compound in pharmaceutical compositions for topical administration is 0.05 to 15% (by weight), preferably 0.02 to 5%, and more preferably 0.1 to 3%.

A method for obtaining a diagnostic image of a host is provided by the present invention. In particular, the method comprises administering to the host a complex of formula (I), (II), or (III), in an amount effective to provide an image; and exposing the host to an energy source, whereupon a diagnostic image of the host is obtained. The diagnostic image can be, for example, a magnetic resonance image, an x-ray contrast image, single photon emission computed spectroscopy (SPECT) image or the like.

For example, a compound of formula (I), (II) or (III), can be complexed with a paramagnetic metal atom and used as a relaxation enhancement agent for magnetic resonance imaging. When administered to a host (e.g., a mammal such as a human), the agent distributes in various concentrations to different tissues, and catalyzes the relaxation of protons in the tissues that have been excited by the absorption of radiofrequency energy from a magnetic resonance imager. This acceleration of the rate of relaxation of the excited protons provides for an image of different contrast when the host is scanned with a magnetic resonance imager. The magnetic resonance imager is used to record images at various times, generally either before and after administration of the agents, or after administration only, and the differences in the images created by the presence of the agent in tissues are used in diagnosis. Guidelines for performing imaging techniques can be found in Stark et al., *Magnetic Resonance Imaging*, Mosbey Year Book: St. Louis, 1992, hereby incorporated by reference.

Accordingly, the present invention provides a method for magnetic resonance imaging of a host (e.g., mammal, such as a human). The method comprises administering to the host a complex of any of formula (I), (II) or (III), in which the metal is paramagnetic, in an amount effective to provide an image; and exposing the host to a magnet, whereupon a magnetic resonance image of the host is obtained. Preferably, a complex used in obtaining a magnetic resonance image comprises Gd. Paramagnetic metal complexes of the present invention are particularly useful as hepatobiliary agents, i.e., for magnetic resonance imaging of the liver and bile ducts.

While the above-described uses for the metal-chelating ligands of the present invention are preferred, those working in the diagnostic arts will appreciate that the ligands also can be complexed with the appropriate metals and used as contrast agents in other imaging techniques, such as x-ray imaging, radionuclide imaging and ultrasound imaging, and in radiotherapy. Accordingly, the present invention further provides a method for x-ray imaging of a host. The method comprises administering to the host a complex of any of formula (I), (II) or (III), in which the metal ion is radio-opaque, in an amount effective to provide an image; and exposing the host to x-rays, whereupon an x-ray contrast image of the host is obtained. The usefulness of metal ions in in vitro and in vivo diagnostic procedures is disclosed in U.S. Pat. No. 4,454,106, hereby incorporated by reference. X-ray contrast imaging procedures can be found in Moss et al., *Computed Tomography of the Body*, W.D. Saunders Company: Philadelphia, 1992; and M. Sovak, Editor, *Radiocontrast Agents*, Springer-Verlag: Berlin, 1984, hereby incorporated by reference.

The most desirable embodiment of this diagnostic process uses $^{111}$In and/or $^{177}$Lu. For example, the radioactive probe $^{111}$In decays with a half life of 2.8 days (67 hours) to an excited state of the daughter nucleus $^{111}$Cd. From this excited state, a cascade of two gamma-rays is emitted, encompassing an isomeric state with a half life of 85 ns. $^{111}$In is useful for single photon emission computed spectroscopy (SPECT), which is a diagnostic tool. Thus, when $^{111}$In (or $^{177}$Lu) is complexed to a compound of formula (I), (II) or (III) and linked to a biomolecule, such as a hapten, which specifically localizes in a tumor, then that particular localization can be three-dimensionally mapped for diagnostic purposes in vivo by SPECT. Alternatively, the emission can be used in vitro in radioimmunoassays. In view of the foregoing, the present invention also provides a method for SPECT imaging of a host (e.g., mammal, such as a human). The method comprises administering to the host a complex of any of formula (I), (II) or (III), in which the metal emits a single photon, in an amount effective to provide an image; and exposing the host to an energy source, whereupon a SPECT image of the host is obtained.

Also provided is a method for treating a cellular disorder in a mammal. The method comprises administering to the mammal (e.g., human) a complex of the present invention in an amount effective to treat the cellular disorder, whereupon the cellular disorder is treated. A preferred complex comprises Pb or Y, in particular $^{90}$Y. The treatment can be prophylactic or therapeutic. By "prophylactic" is meant any degree in inhibition of the onset of the cellular disorder, including complete inhibition. By "therapeutic" is meant any degree in inhibition or any degree of beneficial effects on the disorder in the mammal (e.g., human), e.g., inhibition of the growth or metastasis of a tumor.

Preferably, the method includes administration of a metal complex bound to a hapten having a selective binding site on a cell affected by the disorder. For example, R' can be bound to an mAb, wherein the antibody is directed and created against an epitope found specifically on tumor cells. Thus, when $^{212}$Pb is transported to the antigen site, and subsequently decays in secular equilibrium to $^{212}$Bi and its daughters, a beta irradiation is produced from the lead disintegration. In addition, a beta radiation is produced by the bismuth daughters. This beta radiation is similar to the beta radiation from $^{90}$Y but, in addition, each disintegration of bismuth also produces an alpha particle. In this manner, radiotherapy is provided with a radiation dose from an alpha particle and a beta particle. If desired, only $^{212}$Bi can be introduced in those cases where the disorder to be treated, such as with leukemic cells, can be easily reached within the 1 hour half-life of $^{212}$Bi. Suitable procedures using radiopharmaceuticals can be found in the literature (see, for example, Mettler Jr. et al., *Essentials of Nuclear Medicine Imaging*, Grune and Stratton, Inc.: New York, 1983).

It is possible to use this method to treat cancer, where the cells are widely differentiated. Cancers suitable for treatment with compounds, complexes, and compositions of the invention include, for example, lymphomas, leukemias, colo-rectal cancer, ovarian cancer, breast cancer and prostate cancer. This method might even be preferred where only a long-range beta emitter, such as $^{90}$Y, is desired. In differing environments in vivo, the Bi$^{212}$ is retained inside the chelate after the beta emission in varying amounts. Most desirably, at least 95% of Bi$^{212}$ remains in the metal complex. As much as 80% or 90% of the Bi$^{212}$ can be retained, depending on the medium. In an acidic medium, such as the stomach, at least about 70% of the Bi$^{212}$ is retained.

$^{213}$Bi is a short-lived ($t_{1/2}$=46 min) radionuclide generated from the decay of $^{225}$Ac that emits high energy alpha-particles with an effective range of 0.07-0.10 mm that are ideally suited to treating single-celled neoplasms and micrometastatic carcinomas. Bismuth-labeled HuM195, an anti-CD33 antibody, demonstrated specific and potent cell killing ability when directed against a leukemia cell line (see, for example, Nikula et al., *J. Nucl. Med.*, 1999, 40, 166-176). In addition, the chelating agent N-[2-amino-3-(p-isothiocyanatophen-yl)propyl]-trans-cyclohexane-1,2-diamine-N,N',N',N'',N''-pentaacetic acid was appended to bismuth-labeled J591 mAb to target the external domain of Prostate Specific Membrane Antigen (PSMA) in the treatment of prostate cancer (see, for example, McDevitt et al., *Cancer Res.*, 2000, 60(21), 6095-6100). Therefore, $^{213}$Bi can be complexed to a compound of formula (I), (II) or (III), linked to a biomolecule, such as an mAb, and used to treat cancer, in particular leukemia and prostate cancer, prophylactically or therapeutically.

The following examples further illustrate the invention but, of course, should not be construed as in any way limiting its scope.

EXAMPLES (d)-p-Nitrophenylalanine-(R',R')-trans-1,2-aminocyclohexyl amide dihydrochloride, p-nitro-phenylalanine-2-aminopropylamide and tert-butyloxtcarbonyl-iminodiacetic acid disuccinlmidyl ester were prepared as described in the literature (Wu et al., *Bioorg. Med. Chem.* 5, 1925-1934 (1997); McMurry et al., *Bioconjugate Chem.*, 3, 108-117 (1992)). The tert-butyl bromoacetate was purchased from Fluka (Ronkonkoma, N.Y.). All other reagents were purchased from either Aldrich (Milwaukee, Wis.), Sigma (St. Louis, Mo.), or Fluka and used without further purification. Ion-exchange resins were obtained from Bio-Rad Laboratories (Richmond, Calif.).

$^{1}$H and $^{13}$C nuclear magnetic resonance (NMR) spectra were obtained using a Varian Gemini 300 instrument (Palo Alto, Calif.). Chemical shifts are reported in ppm on a scale relative to tetramethylsilane (TMS), 3,3,3-trimethylsilylpropionate (TSP), or solvent. Proton chemical shifts are annotated as follows: ppm (multiplicity, integral, coupling constant (Hz)). Chemical ionization mass spectra (CI-MS) were obtained on a Finnegan 3000 instrument (San Jose, Calif.). Fast atom bombardment mass spectra (FAB-MS) were acquired on an Extrel 400 (Pittsburgh, Pa.). Exact mass FAB-MS was obtained on a JOEL SX102 spectrophotometer (Peabody, Mass.). The exact mass measurements in FAB were obtained using an accelerating voltage of 10 kV with the samples being desorbed from a matrix using 6 keV xenon atoms. Mass measurements were performed at 10,000 resolution using electric field scans with the sample peak bracketed by two poly(ethylene glycol) reference ions. Elemental analyses were performed by Atlantic Microlabs (Atlanta, Ga.). The high performance liquid chromatography (HPLC) system components (Beckman Instruments, Fullerton, Calif.) were as follows: a pair of 114M pumps, a 165 dual-wavelength variable uv detector, controlled through a 406 analogue interface module, using System Gold software, and a Beckman 4.6×25 cm ultrasphere ODS 5 μm column. A 25 min gradient from 100% 0.05 M Et$_3$N/HOAc to 100% MeOH at 1 mL/min was employed for all HPLC chromatography.

The human colon carcinoma (LS-174T) cell line was grown in supplemented Eagle's minimum essential medium as previously described (see Brechbiel et al., *Inorg Chem.*, 25, 2772 (1986); and Lagunas-Solar et al., *Appl. Radiat. Isot.*, 38, 129-137 (1987)). The human gastric carcinoma cell line (N87) was kindly provided by Dr. Raya Mandler, Metabolism Branch, NCI. The N87 cell line (Jurcic et al., *Advances in Pharmacology*, Vol. 33, (J. T. August, M. W. Anders, F. Murad, J. T. Coyle Eds.) pp 287-314, Academic Press, Inc., New York, (1995)), which expresses high levels of HER2, was maintained in RPMI 1640 (Quality Biologicals, Gaithersburg, Md.) medium, supplemented with 10% fetal bovine serum (FBS) (Gemini Bio-Products, Woodland, Calif.) and 0.01 mM non-essential amino acids (Quality Biologicals, Gaithersburg, Md.).

Example 1

This example demonstrates the synthesis of 1-N-tert-butyloxycarbonyl-5-methyl-9-(p-nitrobenzyl)-3,8,12-trioxo-1,4,7,10-tetraazacyclododecane (2) (FIG. 1).

1,4-Dioxane (3.5 L) was heated to 90° C. in a 5 L 3-necked Morton flask, p-nitro-phenylalanine-2-aminopropylamide (1) (5.32 g, 20 mmol) was dissolved in anhydrous dimethylformamide (DMF) (40 mL) and taken up into a gas-tight syringe. Additional DMF was added to bring the final volume to 50 mL. BOC-iminodiacetic acid disuccinimidyl ester (8.54 g, 20 mmol) was dissolved in DMF and taken up into a gas-tight syringe, and DMF was added to the solution to bring the final volume to 50 mL. The syringes were loaded onto a Sage Model M362 syringe pump (Orion Research, Beverly, Mass.), and the two solutions were added to the hot 1,4-dioxane such that the addition was complete within 24 h. Three more additions of 20 mmol of each reactant were added with a fifth and final addition of 18 mmol over the following 5 d. After completion of the final addition, the reaction was heated for an additional 18 h, and then cooled to room temperature. The reaction was concentrated to a thick oil under vacuum, and the brown residue taken up in $CHCl_3$ (300 mL). Addition of $CHCl_3$ resulted in a suspension of an off-white precipitate, which was collected after cooling, washed with $CHCl_3$, and dried under vacuum. The filtrate was washed with 1 M HCl (2×100 mL), saturated NaCl solution (2×100 mL), 1 M $HCO_3^-$ (2×200 mL) and water (2×200 mL), while adding more $CHCl_3$ (100-150 mL) to counter additional precipitate. This precipitate was also collected by filtration, and after drying over anhydrous $Na_2SO_4$, the $CHCl_3$ solution was reduced to form additional precipitate that was also collected. Thin layer chromatography (TLC) of the crude precipitated material indicated one major product, followed closely by a faint second product ($R_f$=0.14, 0.11, silica gel, 5% MeOH in $CHCl_3$). Extensive silica gel chromatography using a very slow gradient from 0 to 5% MeOH in $CHCl_3$ provided the major product free from the trailing material. No substantial amounts of the minor product could be isolated with which to carry into the rest of the synthesis in parallel.

$^1$H NMR (dmso-$d_6$) δ 1.01 (d, 3H, J=6.6), 1.376, 1.386 (2s, 9H), 2.63-2.86 (m, 1H), 2.938 (dd, 1H, J=13.65, 9.9), 3.02-3.19 (m, 1H), 3.25-3.41 (m, 2H), 3.744 (dd, 1H, J=16.0, 12.0), 3.92-3.98 (m, 1H), 4.02-4.20 (m, 1H), 4.38-4.50 (m, 1H), 7.135 (dt, 1H, J=21.9, 5.4), 7.529 (dd, 2H, J=8.7, 2.4), 7.772 (dd, 1H, J=16.0, 9.0)), 8.138 (d, 2H, J=8.7), 8.561 (d, 1H, J=8.4); $^{13}$C NMR (dmso-$d_6$) δ 17.64, 27.85, 24.83, 34.92 (1C), 42.81, 42.93 (1C), 43.96, 44.17 (1C), 48.99, 49.55 (1C), 49.77, 50.31 (1C), 54.20, 54.31 (1C), 79.68, 123.21, 130.42, 146.19, 146.38, 146.45 (1C), 154.74, 154.88 (1C), 168.68, 168.84 (1C), 168.91, 169.08 (1C), 170.53, 170.67 (1C); FAB-MS (glycerol) m/e 464 ($M^+$+1); Anal. Calcd. for $C_{21}H_{29}N_5O_7$: C, 54.41; H, 6.32; N, 15.11. Found: C, 54.19; H, 6.36; N, 14.95.

Example 2

This example demonstrates the synthesis of 2-methyl-6-p-nitrobenzyl-1,4,7,10-tetraazacyclododecane-tetrahydrochloride (1B4M-cyclen tetrahydrochloride) (3) (FIG. 1).

1,4-Dioxane (200 mL) was chilled in an ice bath and saturated with HCl(g). The product of Example 1 (2), the major isomer, (4.4 g, 9.5 mmol) was added and HCl(g) was bubbled through the reaction mixture for an additional 1 h. The reaction mixture was stirred at room temperature for 18 h. Diethyl ether ($Et_2O$) (approx. 150 mL) was added, and the mixture was chilled in the freezer for 1 d. The precipitate was collected by vacuum filtration and washed with $Et_2O$ (400 mL). The light tan powder was vacuum dried at 60° C. overnight.

The powder was suspended in anhydrous tetrahydrofuran (THF) (50 mL), the flask was chilled in an ice bath, and 1 M $BH_3$.THF (58 mL) was added. The mixture was warmed to room temperature and heated at 50° C. overnight (18 h) with the temperature controlled by an $I^2R$ Thermowatch L7-110SA (Cheltenham, Pa.). Progress of the reaction was monitored by quenching a small aliquot with MeOH and heating the aliquot with conc. HCl for 2 hours, removal of the solvents, and HPLC analysis. After 72 h, the reaction was deemed complete without formation of any aniline side-product, and, after cooling the mixture to room temperature, the reaction was quenched with excess MeOH. The solution was stirred for an additional 24 h, after which it was rotary evaporated to a gummy residue, which was placed under vacuum for 18 h. The residue was taken up in EtOH (120 mL), and, while cooling in an ice bath, was saturated with HCl(g), and then vigorously refluxed for 6 h. After cooling to room temperature, the suspension was cooled at 4° C. for 24 h. The product was collected on a Buchner funnel, washed with ether, and dried under vacuum (2.86 g, 67%).

$^1$H NMR ($D_2O$) δ 1.14-1.53 (m, 3H), 2.80-3.98 (complex m, 16H), 7.50-7.58 (m, 2H), 8.18-8.29 (m, 2H); Anal. HPLC $t_R$=10.37 min; FAB-MS (glycerol) m/e 322 ($M^+$+1); Anal. Calcd. For $C_{16}H_{27}N_5O_2(HCl)_3(H_2O)$: C, 42.81; H, 6.08; N, 15.61. Found: C, 42.71; H, 6.16; N, 15.71.

Example 3

This example demonstrates the synthesis of tetra-tert-butyl 2-methyl-6-p-nitrobenzyl-1,4,7,10-tetraazacyclododecane-1,4,7,10-tetraacetate (1B4M-DOTA-tBu ester) (4) (FIG. 1).

1B4M-cyclen tetrahydrochloride (3) (670 mg, 1.49 mmol), as prepared in Example 2, was dissolved in water (10 mL), and the pH was increased to approximately 13 by addition of solid NaOH. The reddish aqueous layer was extracted with $CHCl_3$ (3×80 mL). The combined yellow $CHCl_3$ layers were reduced to dryness, and dried on a vacuum line (493 mg).

$^1$H NMR ($CDCl_3$) δ 0.91 (m, 3H, —$CH_3$), 2.3-2.9 (m, 20H), 7.30 (d, 2H, Ar); 8.09 (d, 2H, Ar); $^{13}$C NMR ($CDCl_3$) δ 18.47, 39.96, 45.06, 45.37, 45.55, 46.28, 49.74, 53.87, 57.33, 123.57, 129.82, 130.00, 146.58, 147.73; MS (CI/$NH_3$) m/e 332 ($M^+$+1).

The free base of 1B4M-cyclen (484 mg, 1.5 mmol) generated above was dissolved in anhydrous dimethylformamide (DMF) and chilled in an ice bath. Tert-butyl bromoacetate (1.17 g, 6.08 mmol) was added. The reaction was stirred for 45 min and warmed to room temperature. A solution of $Na_2CO_3$ in water (645 mg in 13 mL) was added, and the mixture was stirred for 2 h. Toluene (10 mL) was added, and the mixture was stirred for an additional 3 h. The reaction mixture was poured into a separatory funnel, the aqueous layer was removed, and the orange toluene layer was saved. The aqueous layer was extracted with $CHCl_3$ (2×80 mL), and the $CHCl_3$ layers were combined with the toluene. The combined organic layers were reduced to dryness, and the resulting residue was purified on a silica gel column (2.5 cm×35 cm) and eluted with a gradient of 5-10% MeOH in $CHCl_3$ and finally 10% $NH_4OH$ in MeOH. Early fractions contained high $R_f$ materials and later fractions contained the product, as determined by mass spectrometry. The later fractions containing the product were combined, and the solvent was removed by rotary evaporation to produce an orange foam (501 mg, 42%).

¹H NMR (CDCl₃) δ 0.8 (br, 3H, —CH₃), 1.37, 1.39 (singlets, 36H, tBu), 2.0-4.0 (m, 24H), 7.3 (m, 2H, Ar), 8.07 (m, 2H, Ar); MS (CI/NH₃) m/e 779 (M⁺+1), 801 (M+23); Anal. calcd for $C_{40}H_{67}N_5O_{10}$: C, 61.75H, 8.68; N, 9.00. Found: C, 55.95; H, 8.05; N, 8.11.

Example 4

This example demonstrates the synthesis of 2-methyl-6-(p-nitrobenzyl)-1,4,7,10-tetraazacyclododecane-1,4,7,10-tetraacetic acid (1B4M-DOTA-NO₂) (5) (FIG. 1).

1B4M-DOTA-NO₂-tBu ester (4) (214 mg, 0.275 mmol), as prepared in Example 3, was heated to reflux in conc. HCl (8 mL) for 6 h. The solvent was removed by rotary evaporation. The residue was taken up in H₂O (1-2 mL) and freeze dried to yield the product as orange solid (149 mg, 75%).

¹H NMR (D₂O pH 1.5) δ 1.2 (m, 3H, —CH₃), 3.0-4.2 (m, 24H), 7.59 (m, 2H, Ar), 8.26 (d, 2H, Ar); ¹H NMR (D₂O pH 14) δ 0.55, 0.7, 0.8 (three d, 3H, —CH₃), 2.2-3.6(m, 24H), 7.4 (m, 2H, Ar), 8.18 (d, 2H, Ar); MS (CI/NH₃) m/e 554 (M⁺+1); HPLC $t_R$=11.6 min; Anal. calcd for $C_{24}H_{35}N_5O_{10}$·4HCl·H₂O: C, 40.18; H, 5.76; N, 9.76. Found: C, 40.76; H, 5.68; N, 9.79.

Example 5

This example demonstrates the synthesis of 2-methyl-6-(p-aminobenzyl)-1,4,7,10-tetraazacyclododecane-1,4,7,10-tetraacetic acid (1B4M-DOTA-NH₂) (6) (FIG. 1).

A Schlenk flask was charged with 10% Pd/C (28.9 mg) and H₂O (5 mL) and fitted onto an atmospheric hydrogenator. The apparatus was flushed with H₂(g) twice to saturate the catalyst. A solution of 1B4M-DOTA-NO₂ (5) (104 mg, 0.188 mmol), as prepared in Example 4, in H₂O (5 mL) was injected via syringe into the flask. The hydrogenation was allowed to proceed until the uptake of H₂(g) ceased. The reaction mixture was filtered through a bed of Celite 577 on a medium glass fritted funnel. The filtrate was reduced to dryness by rotary evaporation, and the residue was taken up in water (1-2 mL). The solution was lyophilized to give the aniline as a solid (87 mg, 88%).

¹H NMR (D₂O pH 1.5) δ 1.1 (m, 3H), 3.0-4.2 (m, 24H), 7.4 (m, 4H); ¹H NMR (D₂O pH 14) δ 0.6, 0.7, 0.9 (m, 3H), 2.2-3.6 (m, 24H), 6.8 (m, 2H), 7.1 (d, 2H); FAB-MS (glyceraol) m/e 524 (M⁺+1); Anal. HPLC $t_R$=8.1 min; HR-FAB M+H⁺ calcd for $C_{24}H_{38}N_5O_8$ 524.2720 found [HR-FAB] m/e=524.2723, error=+0.6 ppm.

Example 6

This example demonstrates the synthesis of 2-methyl-6-(p-isothiocyanatobenzyl)-1,4,7,10-tetraazacyclododecane-1,4,7,10-tetraacetic acid (1B4M-DOTA-NCS) (7) (FIG. 1).

A 1 M solution of SCCl₂ in CHCl₃ (61 μL) was added to a solution of 1B4M-DOTA-NH₂ (6) (35 mg, 0.055 mmol), as prepared in Example 5, in H₂O (0.5 mL) in a 3 dram vial. The mixture was vigorously stirred with a spin vane for 2 h at room temperature. The aqueous layer was transferred with a pipet to a round bottom flask, and the CHCl₃ layer was washed with H₂O (3×0.5 mL). The combined aqueous layers were lyophilized to provide the 1B4M-DOTA-NCS (7) as a yellow solid (28 mg).

¹H NMR (D₂O pH 1.5) δ 1.2 (m, 3H), 2.9-4.2 (m, 24H), 7.4 (m, 4H); ¹H NMR (D₂O pH 14) δ 0.6, 0.7, 0.9 (m, 3H), 2.2-3.6 (m, 24H), 6.8, 7.3 (m, 4H); MS (CI/NH₃) m/e 566 (M⁺+1); HPLC $t_R$=19.7 min (minor), 20.2 min (major), HR-FAB M+H⁺ calcd for $C_{25}H_{35}N_5O_8S$ 566.2285 found [HRFAB] m/e=566.2301, error =+2.9 ppm.

Example 7

Figure 2:
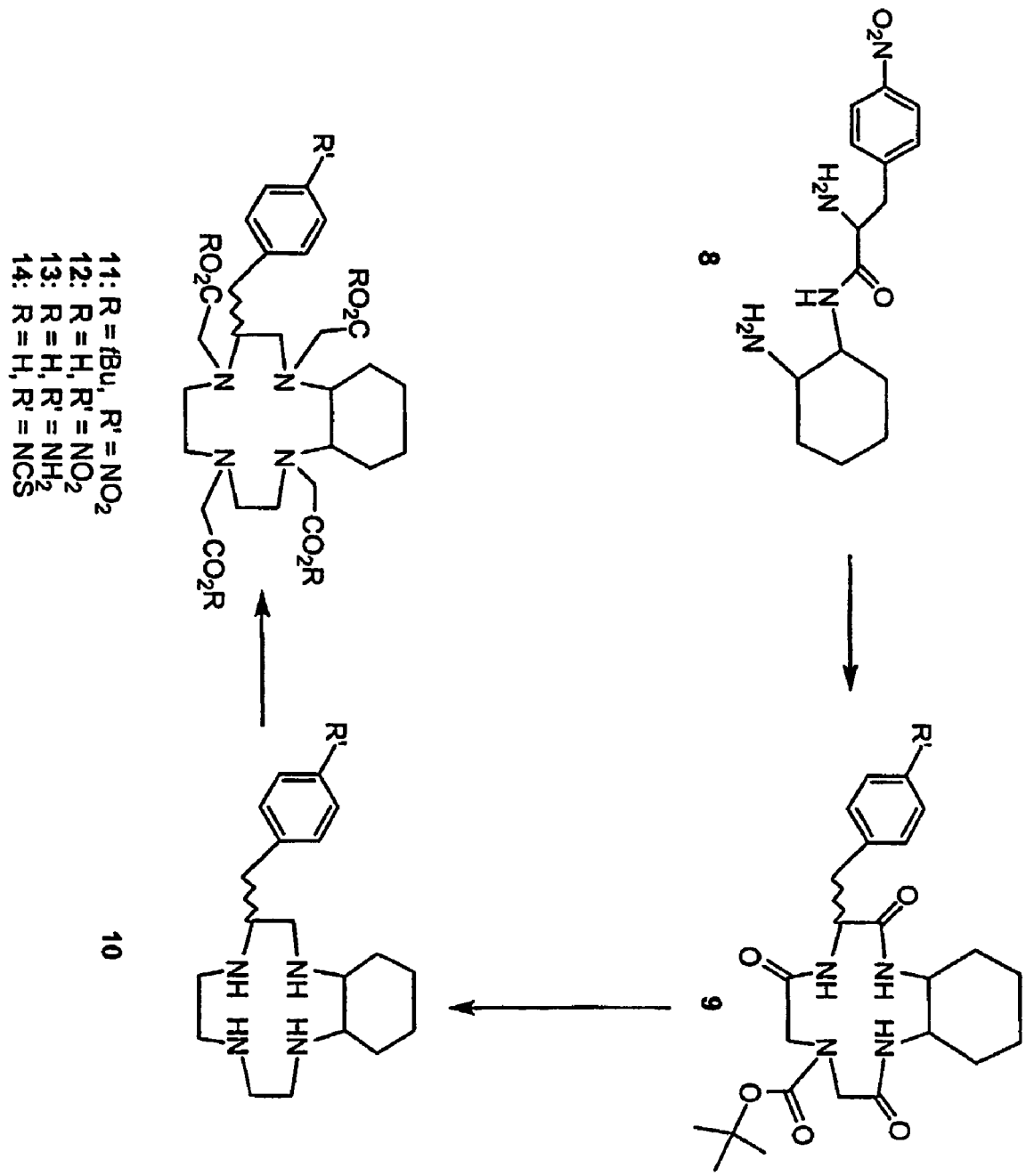
FIG. 2 illustrates the chemical synthesis of 2-p-substituted-benzyl)-5,6-cyclohexano-1,4,7,10-tetraazacyclododecane-1,4,7,10-tetraacetate (Formula II).

This example demonstrates the synthesis of 1-tert-butyloxycarbonyl 3,8,12-trioxo-2-(p-nitrobenzyl)-5,6-cyclohexano-1,4,7,10-tetraazacyclododecane (CHX-cyclen-BOC-triamide) (9) (FIG. 2).

Anhydrous 1,4-dioxane (3.5 L) was heated to 90° C. in a 5 L 3-necked Morton flask, (d)-p-nitrophenylalanine-(R',R')-trans-1,2-aminocyclohexyl amide dihydrochloride (8) (3.79 g, 10 mmol) was dissolved in anhydrous dimethylsulfoxide (DMSO) (35 mL) and Et₃N (3 mL, 22 mmol) was added. The mixture was stirred for 30 min, and the Et₃N/HCl was removed by filtration. The filtrate was taken up into a gas-tight syringe, and additional DMSO was added to bring the final volume up to 50 mL. BOC-iminodiacetic acid disuccinimidyl ester (McMurry et al., *Bioconjugate Chem.* 3, 108-117 (1992)) (4.27 g, 10 mmol) was dissolved in DMF and taken up into a gas-tight syringe, and DMF was added to bring the final volume up to 50 mL. The syringes were loaded onto a Sage Model M352 syringe pump, and the two solutions were added to the hot 1,4-dioxane such that the addition was complete within 24 h. Three more additions of 10 mmol of each reactant were added via syringe pump over the following 5 d. After the fourth addition, the reaction was heated for an additional 18 h and then cooled to room temperature. The reaction was concentrated down to a thick oil under vacuum and the brown residue dissolved in CHCl₃ (100 mL). The CHCl₃ layer was washed with 1 M HCl (2×100 mL), saturated NaCl solution (2×100 mL), 1 M HCO₃— (2×200 mL) and water (2×200 mL). More CHCl₃ (100-150 mL) was added during the extractions. The CHCl₃ layer was dried over anhydrous Na₂SO₄ and filtered, and the filtrate was reduced to dryness by rotary evaporation. The crude product was divided, and each portion was passed over a short silica gel column with 5% MeOH in CHCl₃ for gross purification. All fractions that contained product ($R_f$=0.6, silica gel, 10% MeOH in CHCl₃) were combined. The crude product was only slightly soluble in CHCl₃ and divided into thirds and applied as a slurry to three separate silica gel columns. For this chromatography a slow gradient from 0 to 5% MeOH in CHCl₃ was used. All fractions that contained product were combined, reduced to dryness, and vacuum dried to give the product as a light brown solid (5.89 g, 29%).

¹H NMR (dmso-d₆) δ 1.1-1.5 (m and s, 13H, cyclohexyl and tBu), 1.7-2.0 (m, 4H, cyclohexyl), 3.1-3.3 (m, 3H, cyclen), 3.8-4.4 (m, 6H, cyclen —CH₂Ar), 6.92 (t, 1H, NH), 7.58 (d, 2H, Ar), 8.21 (d, 2H, Ar), 8.34 (d, 1H, NH), 8.57 (dd, 1H, NH); ¹³C NMR (dmso-d₆) δ 24.28, 24.70, 27.86 (tBu), 31.01, 32.41, 35.69, 47.23, 48.20, 49.11, 50.63, 55.30, 56.64, 123.48 (Ar), 130.46(Ar), 146.13 (Ar), 146.55 (Ar), 155.18 (C(O))OtBu), 168.65 (C(O)), 169.56 (C(O)), 171.51 (C(O)); MS (FAB/glycerol) m/e 504 (M⁺+1); analytical HPLC $t_R$=23.4 min; Anal. Calc. for $C_{24}H_{33}N_5O_7$: C, 56.05; H, 6.61; N, 13.91. Found: C, 56.27; H, 6.66; N, 13.55.

Example 8

This example demonstrates the synthesis of 3,8,12-trioxo-2-p-nitrobenzyl)-5,6-cyclohexano-1,4,7,10-tetraazacyclododecane hydrochloride (CHX-cyclen triamide hydrochloride).

1,4-Dioxane (80 mL) was chilled in an ice bath and saturated for 2 h with HCl(g). Compound 9 (3.11 g, 6.2 mmol) was added, and HCl(g) was bubbled through the reaction mixture for an additional 1 h. The reaction mixture was stirred at room temperature for 18 h. Et$_2$O (approx. 150 mL) was added, and the mixture was chilled in the freezer for 1 d. The precipitate was collected by vacuum filtration and washed with Et$_2$O (400 mL). The light brown powder was vacuum dried at 60° C. overnight (2.78 g, 90%).

$^1$H NMR (dmso-d$_6$) δ 1.26 (m, 4H, cyclohexyl), 1.70 (m, 4H, cyclohexyl), 3.10 (d, 2H, J=8.1), 3.45 (s, 7H), 3.80 (m, 4H) 4.2 (m, 2H, —CH$_2$Ar), 7.03 (d, 1H, J=7.8, NH), 7.56 (d, 2H, J=9.0, Ar), 8.16 (d, 2H, J=9.0, Ar), 8.60 (d, 1H, J=9.6, NH), 9.14 (d, 1H, J=7.2, NH); $^{13}$C NMR (dmso-d$_6$) δ 24.27, 24.58 (cyclohexyl) 31.20, 32.35, 35.45, 44.98, 45.40, 50.93, 54.27 (cyclen backbone), 57.06 (—CH$_2$Ar), 123.48, 130.64, 145.94, 146.61 (Ar), 165.31, 165.62, 171.08 (C(O)); MS (FAB/glycerol) m/e 404 (M$^+$+1); analytical HPLC t$_R$=20.8 and 25.3; Anal. calcd for C$_{19}$H$_{25}$N$_5$O$_5$.HCl.H$_2$O: C, 49.84; H, 6.16; N, 15.29. Found: C, 49.60; H, 6.00; N, 15.16.

Example 9

This example demonstrates the synthesis of 2-p-nitrobenzyl)-5,6-cyclohexano-1,4,7,10-tetraazacyclododecane hydrochloride (CHX-cyclen) (10) (FIG. 2).

The product prepared in Example 8 (820 mg, 1.79 mmol) was combined with anhydrous THF (30 mL), the flask was chilled in an ice bath, and 1 M borane in THF (15 mL, 15 mmol) was added. The mixture was warmed to room temperature and heated at 50° C. overnight (18 h). The reaction mixture was added dropwise to MeOH (200 mL), and the solution was reduced to dryness. The yellow solid was transferred to a 250 mL round bottom flask with absolute EtOH (50 mL) and chilled in an ice bath. HCl(g) was bubbled through the reaction mixture for 2 h, and the mixture was heated to reflux for 12 h. Et$_2$O (approx. 150 mL) was added, and the mixture was chilled in the freezer overnight. The hydroscopic pale green-yellow precipitate was collected by suction filtration, washed with Et$_2$O, and vacuum dried (650 mg, 72%).

$^1$H NMR (D$_2$O, pH=1) δ 1.4-2.0 (m, 7H), 2.0-4.2 (m, 16H), 7.68 (m, 2H, Ar), 8.32 (m, 2H, Ar); analytical HPLC t$_R$=15.1 min; MS (CI/NH$_3$) m/e 362 (M$^+$+1); C$_{19}$H$_{31}$N$_5$O$_2$.3.5HCl.H$_2$O: C, 45.00; H, 7.25; N, 13.81. Found: C, 45.93; H, 7.20N, 13.24.

Example 10

This example demonstrates the synthesis of tetra-tert-butyl 2-p-nitrobenzyl)-5,6-cyclohexano-1,4,7,10-tetraazacyclododecane-1,4,7,10-tetraacetate (CHX-DOTA-tBu-ester) (11) (FIG. 2).

The CHX-cyclen salt (10) (650 mg), as prepared in Example 9, was dissolved in water (10 mL), and the pH was raised to about 13 with NaOH pellets. The aqueous layer was extracted with CHCl$_3$ (3×50 mL). The combined CHCl$_3$ layers were dried over anhydrous Na$_2$SO$_4$ and filtered, and the filtrate was reduced to dryness. The yellow solid was vacuum dried (492 mg, approx. 100%).

$^1$H NMR (CDCl$_3$) δ 0.9-1.3 (m, 6H), 1.7 (m, 4H), 1.8-3.0 (m, 17H), 7.37 (d, 2H, Ar), 8.15 (d, 2H, Ar); $^{13}$C NMR (CDCl$_3$) δ 24.97, 25.27, 30.98, 32.26, 39.72, 43.55, 46.40, 47.13, 47.56, 48.47, 57.82, 60.97, 123.39, 130.07, 146.40, 147.73; MS (CL/NH$_3$) m/e 362 (M$^+$+1).

The free base of 10 (473 mg, 1.31 mmol) was dissolved in DMF (5 mL) and chilled in an ice bath. Tert-butyl bromoacetate (1.04 g, 5.33 mmol) was added and the reaction mixture stirred for 30 min. A solution of Na$_2$CO$_3$ in water (557 mg/1 1 mL) was added, and the solution was stirred for 1.5 h. Toluene (5 mL) was added, and the reaction mixture was stirred for another 2.5 h. The reaction mixture was poured into a separatory funnel, the aqueous layer was drained, and the orange toluene layer was saved. The aqueous layer was extracted with CHCl$_3$ (2×40 mL), and the CHCl$_3$ layers were combined with the toluene. The combined organic layers were reduced to dryness. The resulting residue was purified on two consecutive silica gel column (2.5 cm×35 cm) and eluted with 5% MeOH in CHCl$_3$. Early fractions contained high R$_f$ materials and middle fractions (R$_f$=0.54) contained the product. These were combined, and the solvent was removed by rotary evaporation to yield the product as an orange oil (450 mg, 42%).

$^1$H NMR (dmso-d$_6$) δ 1.46 (m, 44H, tBu, cyclohexyl), 1.6-3.6 (m, 23H, macrocycle, —CH2COOtBu, —CH$_2$Ar), 7.43 (d, 1H, J=8.7 Ar), 7.78 (d, 1H, J=7.8, Ar), 8.14 (d, 1H, J=8.7, Ar), 8.20 (d, 1H, J=8.7, Ar); $^{13}$C NMR (dmso-d$_6$) δ 22.42, 22.90, 23.63, 24.36, 25.21, 31.34, 32.01, 43.12, 44.46, 47.98, 48.28, 50.71, 51.80, 52.05, 55.51, 55.63, 61.28, 62.25, 81.49, 81.61, 81.80, 123.63, 130.00, 130.43, 146.28, 148.58, 172.63, 172.93, 173.11; MS (CI/NH$_3$) m/e 818 (M+H$^+$).

Example 11

This example demonstrates the synthesis of 2-p-nitrobenzyl)-5,6-cyclohexano-1,4,7,10-tetraazacyclododecane-1,4,7,10-tetraacetic acid (CHX-DOTA-NO$_2$) (12) (FIG. 2).

CHX-DOTA-tBu ester (11) (450 mg, 0.55 mmol), as prepared in Example 10, was refluxed in conc. HCl (aq) (10 mL) for 6 h. The solvent was removed by rotary evaporation. The residue was added to water (1-2 mL) and freeze dried. The product was isolated as a light brown solid (390 mg, 94%).

$^1$H NMR (D$_2$O, pH=1.5) δ 1.2-2 (m, 8H, cyclohexyl), 2-4.2 (m, 23H, cyclen, —CH$_2$COOH, —CH$_2$Ar), 7.55 (d, 2H, J=8.7, Ar), 8.25 (d, 2H, J=9, Ar); MS (CI/NH$_3$) m/e 594 (M$^+$+1), 616 (M$^+$+23); HPLC t$_R$=13.3 min; Anal. calcd for C$_{27}$H$_{39}$N$_5$O$_{10}$.4HCl.H$_2$O: C, 42.81; H, 5.99; N, 9.25. Found: C, 42.62; H, 5.93; N, 9.18.

Example 12

This example demonstrates an alternate purification method of 2-(p-nitrobenzyl)-5,6-cyclohexano-1,4,7,10-tetraazacyclododecane-1,4,7,10-tetraacetic acid (CHX-DOTA-NO2) (12) (FIG. 2).

Tetra-amine 11 (1.55 g, 3.06 mmol) was alkylated as described above. The crude ester was treated with trifluoroacetic acid (50 mL) for 18 h. After elimination of the acid by rotary evaporation, the residue was dried under vacuum for 24 h. The residue was taken up in minimal H$_2$O, loaded onto a cation ion-exchange resin (2.6×30 cm, AG50wX8, 200-400 mesh, H+ form) and washed with H$_2$O until the eluant was above pH 5. The crude product was eluted from the column with 2 M NH$_4$OH (1 L). The basic solution was rotary evaporated to leave the crude product as a brown solid after drying under vacuum for 24 h. This material was taken up in minimal H$_2$O and loaded onto an anion ion-exchange resin column (1.6×30 cm, AG1x8, 200-400 mesh, HOAc form) and eluted with a 01.5 M HOAc linear gradient (2 L total) collected in 18×150 test tubes. The reaction by-product arising from trialkylation as determined by FAB-MS was eluted first (tubes 10-17), while the tetraacetic acid product eluted later (tubes 25-36). The contents of the tubes were combined and concentrated to about 50 mL, after which the product was isolated as a white powder after lyophilization (860 mg, 47%).

This product was identical in all regards to that isolated as the tetra-ester followed by acidic deprotection of the esters.

Example 13

This example demonstrates the synthesis of 2-(p-aminobenzyl)-5,6-cyclohexano-1,4,7,10-tetraazacyclododecane-1,4,7,10-tetraacetate (CHX-DOTA-NH$_2$) (13) (FIG. 2).

A Schlenk flask was charged with 10% Pd/C (29 mg) and H$_2$O (5 mL) and fitted onto an atmospheric hydrogenator. The apparatus was flushed with H$_2$(g) two times in order fully saturate the catalyst. A solution of CHX-DOTA-NO$_2$ (12) (102 mg, 0.13 mmol), as prepared in Example 11, in H$_2$O (5 mL) was injected via syringe into the flask. The hydrogenation was allowed to proceed until the uptake of H$_2$(g) ceased. The reaction mixture was filtered through a bed of Celite 577 packed in a medium glass fritted funnel. The filtrate was reduced to dryness by rotary evaporation, and the residue was taken up in water (1-2 mL). The resulting solid was lyophilized to give the aniline as a pale yellow solid (97 mg, approx. 100%).

$^1$H NMR (D$_2$O, pH=1.5) δ 1.2-2.0 (m, 8H), 2.0-4.2 (m, 23H), 7.44 (m, 4H); $^1$H NMR (D$_2$O, pH=14) δ 0.8-1.8 (m, 8H), 1.8-3.6 (m, 23H), 6.83 (m, 2H), 6.08 (m, 2H); FAB-MS (glycerol) m/e 564 (M$^+$+1); HPLC $t_R$=15.8 min; HR-FAB M+H$^+$ calcd for C$_{27}$H$_{41}$N$_5$O$_8$Na 586.2853 found [HRFAB] m/e=586.2841, error=-2.1 ppm.

Example 14

This example demonstrates the synthesis of 2-(p-isothiocyanatobenzyl)-5,6-cyclohexano-1,4,7,10-tetraazacyclododecane-1,4,7,10-tetraacetate (CHX-DOTA-NCS) (14) (FIG. 2).

A 1 M solution of SCCl$_2$ in CHCl$_3$ (55 μL) was added to a solution of CHX-DOTA-NH$_2$ (13) (30.5 mg, 0.049 mmol), as prepared in Example 13, in H$_2$O (0.5 mL) in a 3 dram vial. The mixture was stirred rapidly for 2 h at room temperature. The aqueous layer was decanted with a pipet into a round bottom flask, and the CHCl$_3$ layer was washed with H$_2$O (3×0.5 mL). The combined aqueous layers were lyophilized to give CHX-DOTA-NCS (14) as a yellow solid (34.6 mg, 94%).

$^1$H NMR (D$_2$O, pH=1) δ 1-1.6 (m, 4H), 1.6-2.0 (m, 3H), 2.0-2.6 (m, 5H), 2.-4.0 (m, 18H), 7.38-7.51 (m, 4H, Ar); $^1$H HNMR (D$_2$O, pH=14) δ 0.8-1.4 (m, 4H), 1.4-3.7 (m, 27H), 7.16-7.31 (m, 4H, Ar); MS (FAB/glycerol) m/e 606 (M$^+$+1); IR (Nujol) 2150 cm$^{-1}$; HPLC $t_R$=20.9 and 21.45 min; M-H$^+$ calcd for C$_{28}$H$_{38}$N$_5$ O$_8$S 604.2441 found [HRFAB] m/e=604.2448, error =+1.2 ppm.

Example 15

This example demonstrates the conjugation of HERCEPTIN with C-DOTA, PA-DOTA, 1B4M-DOTA (7), and CHX-DOTA (14).

The HERCEPTIN was generously provided by Dr. R. Altemus (Radiation Oncology Branch, NCI). The HERCEPTIN was concentrated to 5 mg/mL and conjugated with either 2-(p-isothiocyanatobenzyl)-1,4,7,10-tetraazacyclododecane-1,4,7,10-tetraacetic acid (C-DOTA), 1,4,7,10-tetraaza-N-(1-carboxy-3-(4-nitrophenyl)propyl)-N',N'',N'''-tris(acetic acid) cyclododecane (PA-DOTA), 1 B4M-DOTA (7), or CHX-DOTA (14), employing the linkage methods for aryl isothiocyanato groups that have been well described in the literature (see, for example, Mirzadeh et al., Bioconjugate Chem. 1, 59-65 (1990)). Unreacted or "free" ligand was separated from the conjugated antibody by dialysis in 0.15 M NH$_4$OAc. The average number of chelates per antibody for the conjugation products was about 1 chelate per protein moiety, as determined by the appropriate spectrometric method for these chelating agents (Dadachova et al., Nuci. Med. Biol. 26, 977-982 (1999); Pippin et al., Bioconjugate Chem. 3, 342-345 (1992)). Protein concentration was determined using the Lowry method with a standard of bovine serum albumin (Lowry et al., J Biol. Chem., 193, 265-275 (1951)).

Example 16

This example demonstrates radiolabeling and comparative radiolabeling of the C-DOTA-, PA-DOTA-, 1B4M-DOTA (7)-, and CHX-DOTA (14)-HERCEPTIN immunoconjugates prepared in Example 15.

Figure 3:
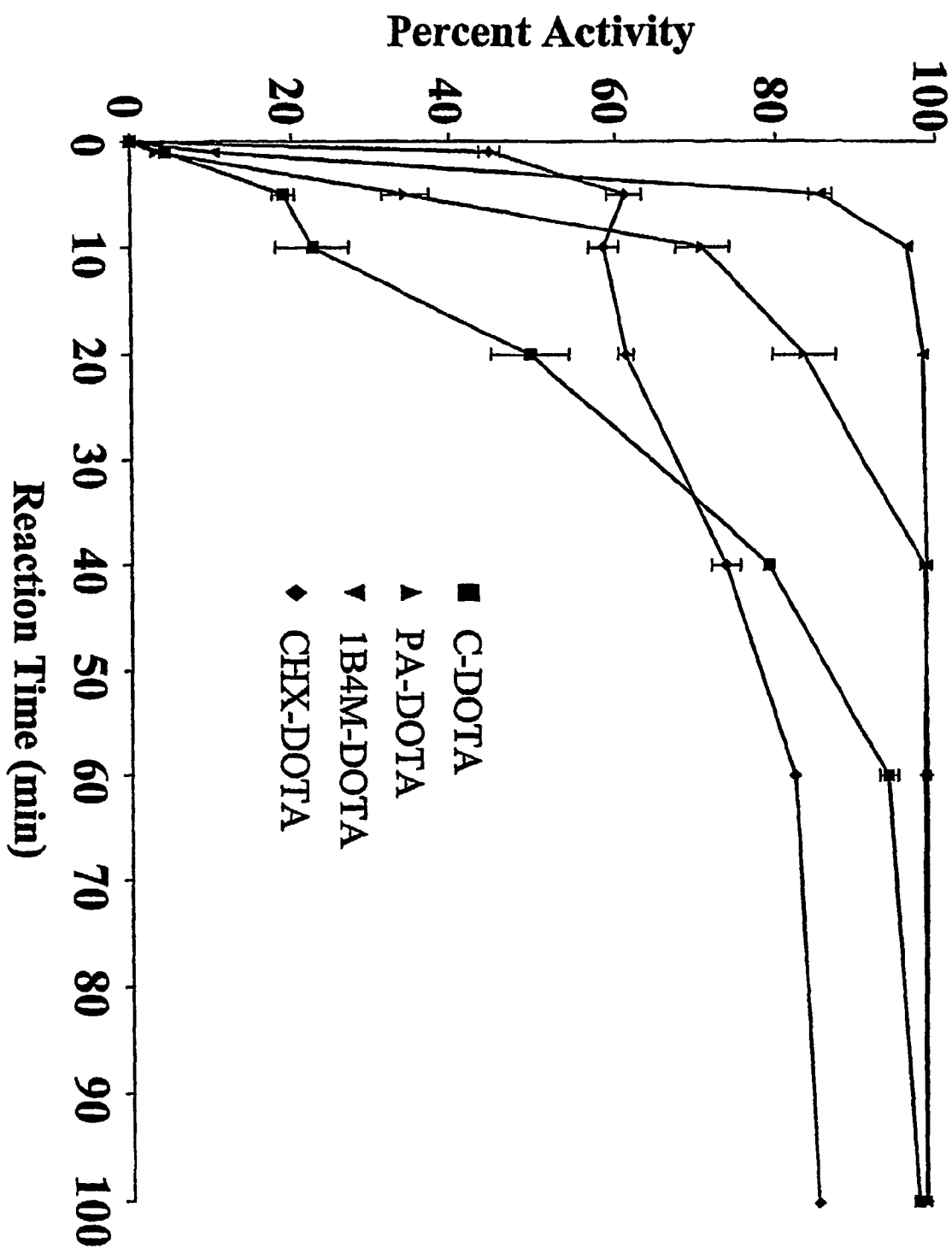
FIG. 3 is a line graph depicting the radiolabeling formation kinetics of $^{177}$Lu DOTA-HERCEPTIN™ radioimmunoconjugates.

Radiolabeling with $^{177}$Lu of the four immunoconjugates was performed analogously to previous reports (see, for example, Ruegg et al., Cancer Res. 50, 422 1-4226 (1990)). The $^{177}$Lu (1-3 mCi in 10-20 μL 0.1 M HCl) (U. Missouri, Columbia) was added to about 200 μL 0.15 M NH$_4$Ac buffer (pH 5.0-5.5) containing 300-400 μg of each of the DOTA-HERCEPTIN immunoconjugates prepared in Example 15. The reaction mixtures were incubated at 37° C. for 1-2.5 h. The reaction kinetics were followed by taking aliquots at different times and analyzing the components using ITLC developed in 10 mM EDTA/0.15 M NH$_4$OAc (FIG. 3). The reactions were halted by adding 5 μL of 0.1 M DTPA. The reaction yields were determined by the ITLC method described previously (Ma et al., Nucl. Med Biol., 29, 91-105 (2002)). The $^{177}$Lu-DOTA-HERCEPTIN conjugates were purified through a 10-DG desalting column (Bio-Rad, Hercules, CA) eluted using PBS and the antibody peaks were collected. Purity of the $^{177}$Lu radiolabeled DOTA-HERCEPTTN radiolabeled immunoconjugates was determined using ITLC and/or size exclusion HPLC (SE-HPLC).

Radio-iodination of HERCEPT with Na $^{125}$I was performed as described using the Iodogen method (Fraker et aL, Biochem. Biophys. Res. Commun., 80, 849-857 (1978)). The product was purified using a desalting column (PD-10; Amersham Biosciences, Piscataway, NJ).

Example 17

This example demonstrates an immunoreactivity assay for the four radioimmunoconjugates (RICs) prepared in Example 16.

The immunoreactivity of the RIC was assessed in a live-cell radioimmunoassay (RIA) as detailed elsewhere (Garmestani et al., Nuci. Med. Biol., 29, 599-606 (2002)). HER2 positive cells (N87) were harvested, pelleted at 1,000×g (Allegra 6KR; Beckman Coulter, Palo Alto, Calif.) and resuspended in PBS (pH 7.2) containing 1% BSA and were added to 12×75 mM polypropylene tubes (1×10$^6$ cells in 100 μL). Serial dilutions of the radiolabeled HERCEPTIN preparations (about 200,000 cpm -12,500 cpm in 50 μL) were then added in duplicate and gently shaken. Following an overnight incubation at 4° C., the cells were washed once with 4 mL of 1% BSA in PBS and pelleted at 1,000×g for 5 min, and the supernatant was decanted. The pelleted cells were then counted in a γ-scintillation counter (Packard), and the percent binding was calculated for each dilution. The values presented in Table 1 are an average of the serial dilutions. To confirm the specific reactivity of the RIC, cells were incubated with about 200,000 cpm of the RIC along with an excess (10 µg) of unlabeled HERCEPTIN.

TABLE 1

Radioimmunoassay data for studied radioimmunoconjugates

| Conjugate | HER2 + | HER2 − | Spec Activity (µCi/µg) |
|---|---|---|---|
| C-DOTA | 50.8 | 7.1 | 7.2 |
| PA-DOTA | 43.1 | 8.8 | 16.5 |
| 1B4M-DOTA (7) | 47.2 | 6.7 | 13.7 |
| CHX-DOTA (14) | 45.8 | 4.3 | 14.8 |
| $^{125}$I | 58.5 | 11.2 | 5.7 |

Example 18

This example demonstrates in vitro stability of the immunoconjugates prepared in Example 16.

Figure 4:
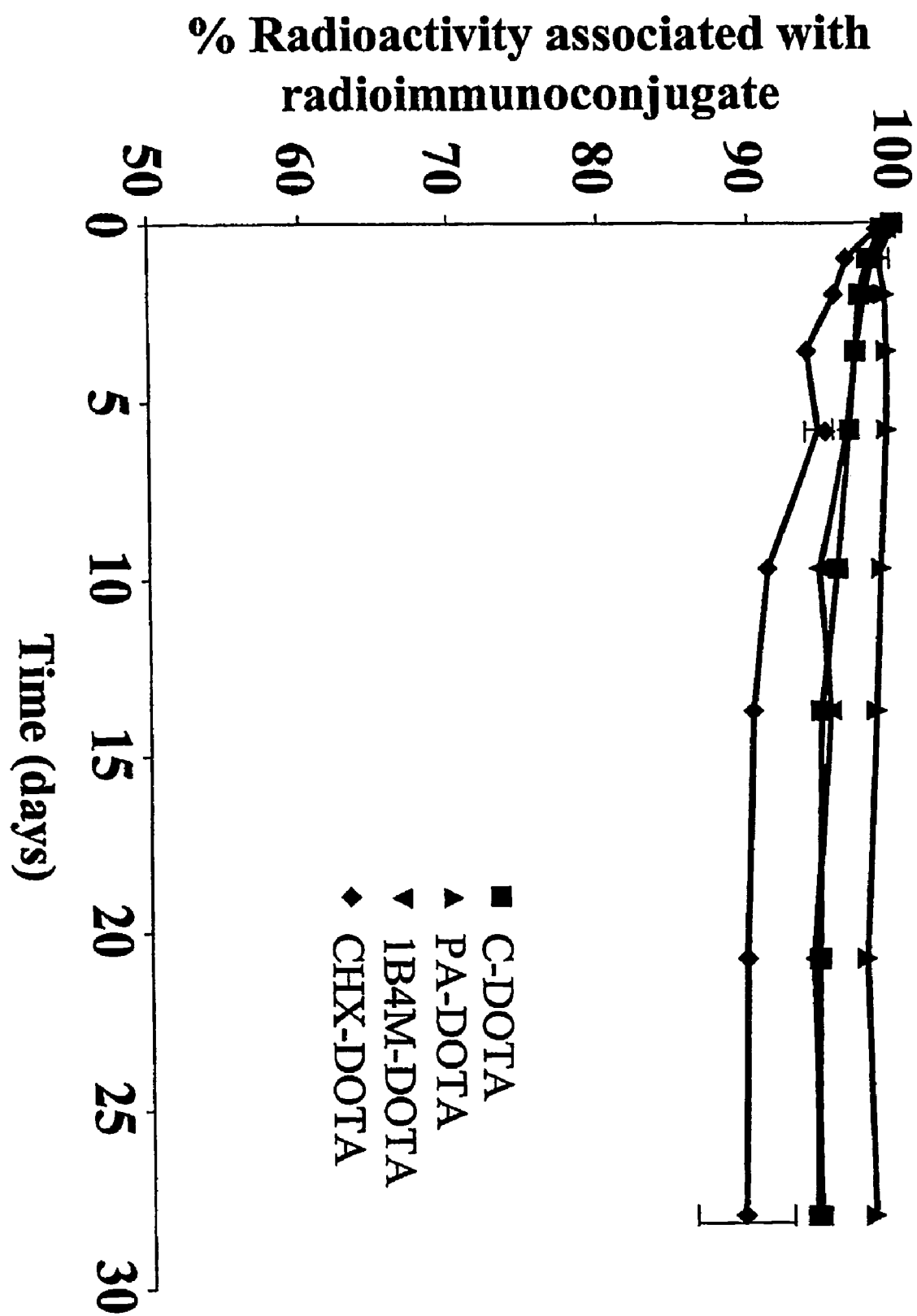
FIG. 4 is a line graph depicting the in vitro serum stability as measured by instant thin layer chromatography (ITLC) of $^{177}$Lu DOTA-HERCEPTIN radioimmunoconjugates.

An in vitro serum stability study was performed with all four of the above radioimmunoconjugates prepared in Example 16 with the measurements being determined by ITLC and size exclusion high performance liquid chromatography (SE-HIPLC) methods over two months. The purified $^{177}$Lu-DOTA-HERCEPTIN conjugates (2 mL each) were mixed with 2 mL human serum (Gemini Bioproducts, Woodland, Calif.). The mixtures were maintained in a 5% $CO_2$ incubator at 37° C. At different time points, 50 µL aliquots were taken, mixed with 5 µL of 0.1 M DTPA, and incubated at 37° C. for 30 min. The percentage of $^{177}$Lu associated with the immunoconjugate was analyzed by both ITLC (FIG. 3) and SE-HPLC (FIG. 4). The $^{177}$Lu-DOTA-HERCEPTIN conjugate demonstrated superior stability among the four different DOTA immunoconjugates that were investigated. Both of the $^{177}$Lu-C-DOTA and the 1B4M-DOTA (7)-HERCEPTIN conjugates exhibited similar stability. The $^{177}$Lu-CHX-DOTA (14)-HERCEPTIN conjugate appeared to be less stable.

This example demonstrates in vitro stability of a compound of formula (PIP-DOTA) conjugated to HERCEPTIN and complexed to a radioisotope.

An in vitro serum stability study was performed on piperidinyl-substituted DOTA-HERCEPTIN conjugates, as prepared in Example 15, that were complexed to $^{205}$Bi, $^{153}$Gd or $^{86}$Y, as prepared in Example 16. The purified PIP-DOTA radioimmunoconjugates (2 mL each) were mixed with 2 mL human serum (Gemini Bioproducts, Woodland, Calif.). The mixtures were maintained in a 5% $CO_2$ incubator at 37° C. At different time points, 35 µL ($^{205}$Bi) or 80 µL ($^{153}$Gd and $^{86}$Y) aliquots were taken, mixed with 5 µL of 0.1 M DTPA, and incubated at 37° C. for 30 min. The percentage of $^{205}$Bi, $^{153}$Gd or $^{86}$Y associated with the PIP-DOTA immunoconjugate was analyzed by SE-HPLC. The $^{205}$Bi and $^{153}$Gd conjugates demonstrated superior stability over time.

Example 20

This example demonstrates an in vivo tumor model study and biodistribution study of the radioimmunoconjugates prepared in Example 16.

The radioimmunoconjugates (RICs) were compared in vivo using athymic mice bearing human colon adenocarcinoma xenografts. Female athymic mice (nu/nu), obtained from Charles River Laboratories (Wilmington, Mass.) at 4-6 weeks of age, were injected subcutaneously on the flank with 2×10$^6$ LS-174T cells in 0.2 mL of RPMI-1640. At approximately 10-14 days, when the tumors measured between 0.4-0.6 cm in diameter, the mice received the $^{177}$Lu-labeled HERCEPTIN. The mice were injected with each RIC (about 5 µCi of each) intravenously (i.v.) via the tail vein. Mice (n=5) were sacrificed by exsanguination at 24, 48, 72, 96 and 168 h.

Figure 5:
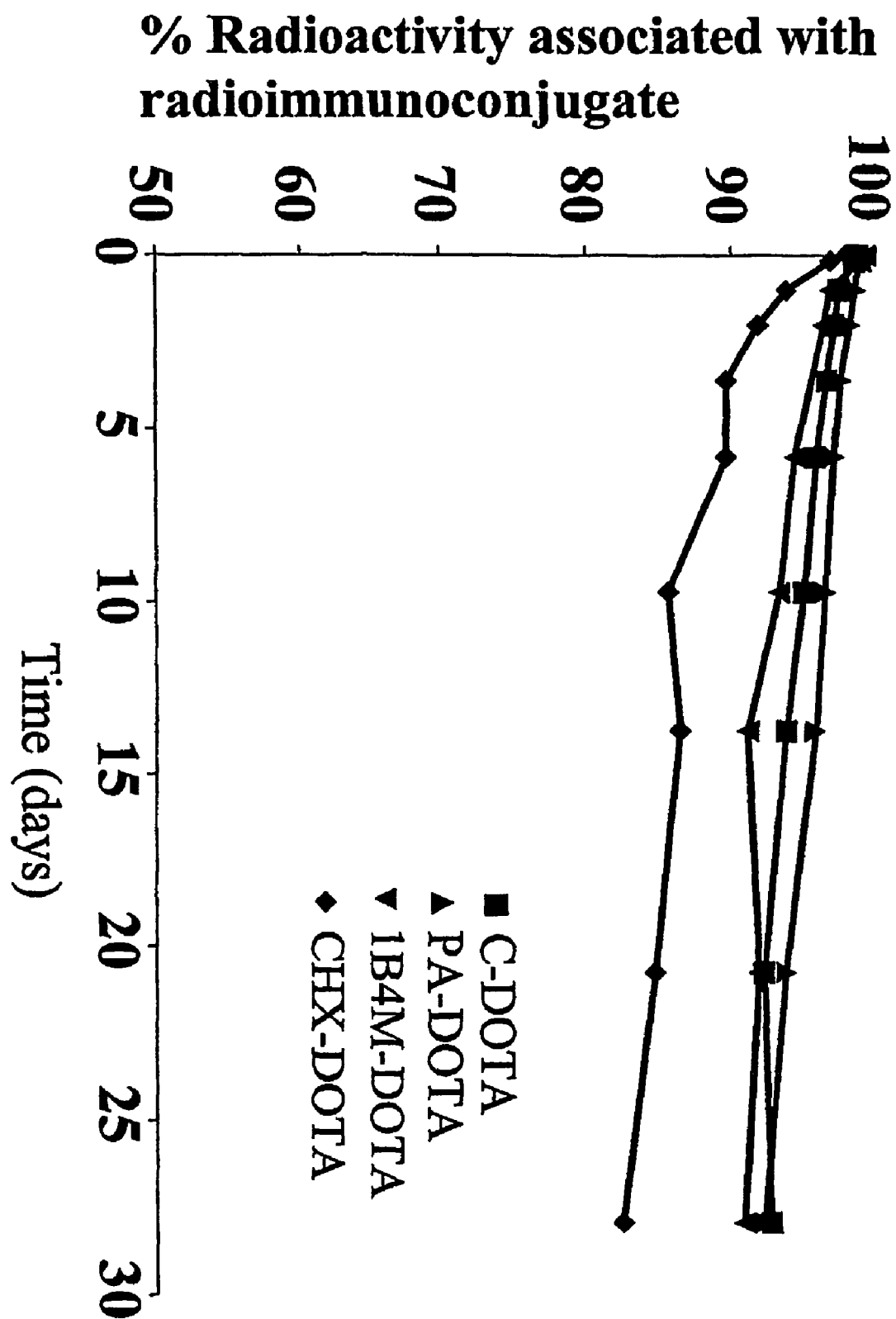
FIG. 5 is a line graph depicting the in vitro serum stability as measured by size exclusion high performance liquid chromatography (SE-HPLC) of $^{177}$Lu DOTA-HERCEPTIN radioimmunoconjugates.

Blood, tumor and the major organs were collected and wet-weighed, and the radioactivity was counted in a γ-counter (Minaxi-γ, Packard, Downers Grove, Ill.). The percent injected dose per gram (% ID/g) was determined for each tissue as well as the radiolocalization indices (% ID/g in tumor divided by the % ID/g in the normal tissue). The mean and average deviation for each tissue was also calculated. Table 2 and FIG. 5 summarize the results.

TABLE 2

Biodistribution of HERCEPTIN ™ radiolabeled with $^{177}$Lu using bifunctional chelates after intravenous injection: Percent Injected dose/gram

| Conjugate | Tissue | Time (h) | | | | |
|---|---|---|---|---|---|---|
| | | 24 | 48 | 72 | 96 | 168 |
| C-DOTA | Blood | 17.22 (1.25)$^a$ | 13.31 (2.75) | 11.62 (1.91) | 11.23 (1.19) | 6.12 (2.17) |
| (comparative) | Tumor | 17.08 (3.36) | 36.31 (12.32) | 37.38 (14.62) | 25.95 (6.76) | 24.64 (5.89) |
| | Liver | 6.63 (1.24) | 8.18 (1.28) | 5.86 (1.01) | 4.84 (0.33) | 4.82 (0.75) |
| | Spleen | 5.93 (0.68) | 6.04 (0.66) | 5.46 (1.37) | 4.59 (0.57) | 4.72 (2.13) |
| | Kidney | 5.20 (0.56) | 5.13 (0.95) | 5.02 (0.77) | 3.68 (0.42) | 2.63 (0.42) |
| | Lung | 6.26 (0.76) | 4.42 (1.92) | 4.58 (0.72) | 4.98 (0.69) | 2.86 (0.78) |
| PA-DOTA | Blood | 13.26 (2.98) | 9.22 (2.60) | 7.70 (1.97) | 4.88 (2.00) | 3.54 (0.90) |
| (comparative) | Tumor | 17.69 (6.23) | 23.85 (7.73) | 32.30 (10.41) | 20.77 (4.11) | 18.15 (7.14) |
| | Liver | 7.66 (0.76) | 7.92 (1.17) | 7.40 (0.91) | 6.87 (2.28) | 5.80 (0.62) |
| | Spleen | 7.24 (1.32) | 7.74 (1.60) | 5.50 (1.22) | 4.47 (0.52) | 4.47 (0.79) |
| | Kidney | 4.38 (0.45) | 3.59 (0.70) | 3.43 (0.7) | 2.91 (0.94) | 1.89 (0.20) |
| | Lung | 5.28 (1.14) | 3.46 (0.82) | 3.23 (0.73) | 2.27 (0.86) | 1.62 (0.27) |
| 1B4M-DOTA | Blood | 13.88 (1.71) | 13.87 (1.17) | 11.65 (1.44) | 10.40 (1.41) | 5.12 (2.88) |
| (7) | Tumor | 17.48 (5.09) | 42.46 (12.35) | 39.22 (6.50) | 27.06 (5.12) | 22.28 (9.81) |
| | Liver | 5.09 (1.11) | 4.48 (0.50) | 5.34 (1.09) | 4.14 (0.98) | 4.79 (0.90) |
| | Spleen | 4.05 (0.62) | 4.19 (0.48) | 5.07 (1.62) | 4.43 (0.64) | 3.33 (0.94) |
| | Kidney | 3.88 (0.29) | 3.94 (0.45) | 4.35 (0.70) | 3.11 (0.31) | 2.40 (0.58) |
| | Lung | 5.58 (0.72) | 4.95 (0.47) | 5.32 (1.09) | 4.21 (0.50) | 2.65 (1.09) |

TABLE 2-continued

Biodistribution of HERCEPTIN™ radiolabeled with $^{177}$Lu using bifunctional chelates after intravenous injection: Percent Injected dose/gram

| Conjugate | Tissue | Time (h) | | | | |
|---|---|---|---|---|---|---|
| | | 24 | 48 | 72 | 96 | 168 |
| CHX-DOTA (14) | Blood | 9.40 (2.11) | 9.60 (0.83) | 7.58 (2.01) | 6.84 (0.92) | 3.82 (1.51) |
| | Tumor | 16.32 (4.94) | 26.78 (3.25) | 24.23 (11.96) | 21.28 (5.51) | 18.14 (9.22) |
| | Liver | 7.80 (0.81) | 5.48 (0.53) | 6.60 (1.07) | 5.71 (0.80) | 6.65 (3.05) |
| | Spleen | 5.67 (2.21) | 4.50 (0.56) | 4.32 (0.69) | 4.03 (0.37) | 3.68 (0.80) |
| | Kidney | 4.87 (0.67) | 4.23 (0.88) | 3.56 (0.36) | 3.22 (0.62) | 2.79 (0.37) |
| | Lung | 4.70 (1.22) | 3.49 (0.33) | 3.72 (1.08) | 3.12 (0.39) | 2.65 (0.83) |
| $^{125}$I | Blood | 12.21 (1.62) | 11.28 (1.18) | 9.55 (1.67) | 8.28 (1.14) | 5.44 (1.80) |
| | Tumor | 12.60 (3.85) | 19.25 (4.44) | 17.33 (5.90) | 12.52 (3.37) | 9.11 (3.87) |
| | Liver | 2.95 (0.46) | 2.58 (0.38) | 2.39 (0.41) | 1.87 (0.28) | 1.40 (0.43) |
| | Spleen | 3.21 (0.64) | 2.76 (0.35) | 2.34 (0.63) | 1.91 (0.30) | 1.31 (0.48) |
| | Kidney | 2.73 (0.35) | 2.48 (0.47) | 2.21 (0.39) | 1.61 (0.26) | 1.19 (0.33) |
| | Lung | 5.39 (0.90) | 4.14 (0.75) | 4.05 (0.79) | 3.58 (0.47) | 2.42 (0.70) |

$^a$The values represent the average % ID/g (percent injected dose/gram); values in parentheses are the average deviation of the % ID/g.

Differences in the liver-to-blood and spleen-to-blood ratios are evident. Each of the C-DOTA, 1B4M-DOTA (7) and CHX-DOTA (14) conjugates shows an increase in the liver-to-blood ratios, with CHX-DOTA (14) demonstrating the greatest increase that does not occur until 168 h. In contrast, the PA-DOTA exhibits a steady increase in the liver-to-blood ratio throughout the study period with an initial ratio of 0.62 at 24 h, peaking at 96 h with 1.91, and declining slightly to 1.77 by 168 h.

Differences were also found between the PA-DOTA and the other three RIC in the spleen-to-blood ratios. Again, in this instance, the ratios obtained for the C-DOTA, 1B4M-(7) DOTA and CHX-(14) DOTA are relatively stable and less than 1 from 24 to 96 h. It is not until the 168 h time point that an increase is observed in the ratios. In contrast to this pattern, the RIC constructed with the PA-DOTA ligand begins an increase in the spleen-to-blood ratio at 96 h.

The CHX-DOTA (14) RIC resulted in the highest values throughout the study. At 24 h, the femur % ID/g is 3.52±0.67, which then peaks at 96 h at 4.04±0.88. In contrast, the RIC consisting of the PA-DOTA ligand yielded the lowest femur % ID/g with 1.98±0.17, which declined to 0.97±0.17 and 1.04±0.16 at 96 and 168 h, respectively. The $^{177}$Lu-C-DOTA and 1B4M-DOTA (7) HERCEPTIN conjugates were not appreciably different from each other, and both were intermediate in the femur % ID/g as compared to the CHX- and PA-DOTA RIC. Differences among the $^{177}$Lu-labeled RIC were also evident in the % ID/g calculated for the tumor xenografts and the other normal tissues that were collected (Table 2).

The greatest uptake in tumor by a RIC was observed with the $^{177}$Lu-1B4M-DOTA (7) HERCEPT. At 48 and 72 h the tumor % ID/g was 42.46±12.35 and 39.22±6.50 respectively. The lowest values 26.78±3.25 and 24.23±11.96, were obtained with the CHX-DOTA (14) RIC at the same time points.

Among the normal tissues, the liver presents with the highest % ID/g for each of the RIC. The CHX-DOTA (14) has the highest initial value (7.80±0.81) at 24 h, which declines to 5.48±0.53 at 48 h and then fluctuates, ending with the highest value at 168 h (6.65±3.05) of the RICs. The conjugate containing the PA-DOTA has an initial value of 7.66±1.17 at 24 h, which peaks at 48 h (7.92±1.17) and then declines to 5.80±0.62 by 168 h. The C-DOTA RIC has a similar profile, in which the liver % ID/g peaks at 48 h (8.18±1.28) and decreases to 4.82±0.75 at 168 h. The conjugate containing the 1B4M-DOTA (7) RIC resulted in the lowest liver % ID/g values throughout the entire study period.

In other normal tissues, the C-DOTA RIC resulted in the highest kidney % ID/g at each of the study time points with the exception of 168 h, at which a value of 2.79±0.37 was obtained with the CHiX-DOTA (14) RIC. The spleen % ID/g was the greatest with the PA-DOTA RIC from 24-72 h, while higher values were determined at 96 and 168 h with the C-DOTA RIC. The lowest spleen % ID/g values were obtained with $^{177}$Lu-1B4M-DOTA-HERCEPTIN at 24, 48 and 168 h and with the CHX-DOTA (14) RIC at 72 and 96 h.

The blood pharmacokinetics were also determined for the radioimmuno-conjugates prepared in Example 16. Following injection of the radioimmunoconjugates (n=5), blood samples were collected at various time points via the tail vein in heparinized capillary tubes (10 µL). The blood was transferred to a tube, and the radioactivity was measured in a γ-counter. The percent injected dose per mL of blood was calculated for each of the samples.

Figure 6:
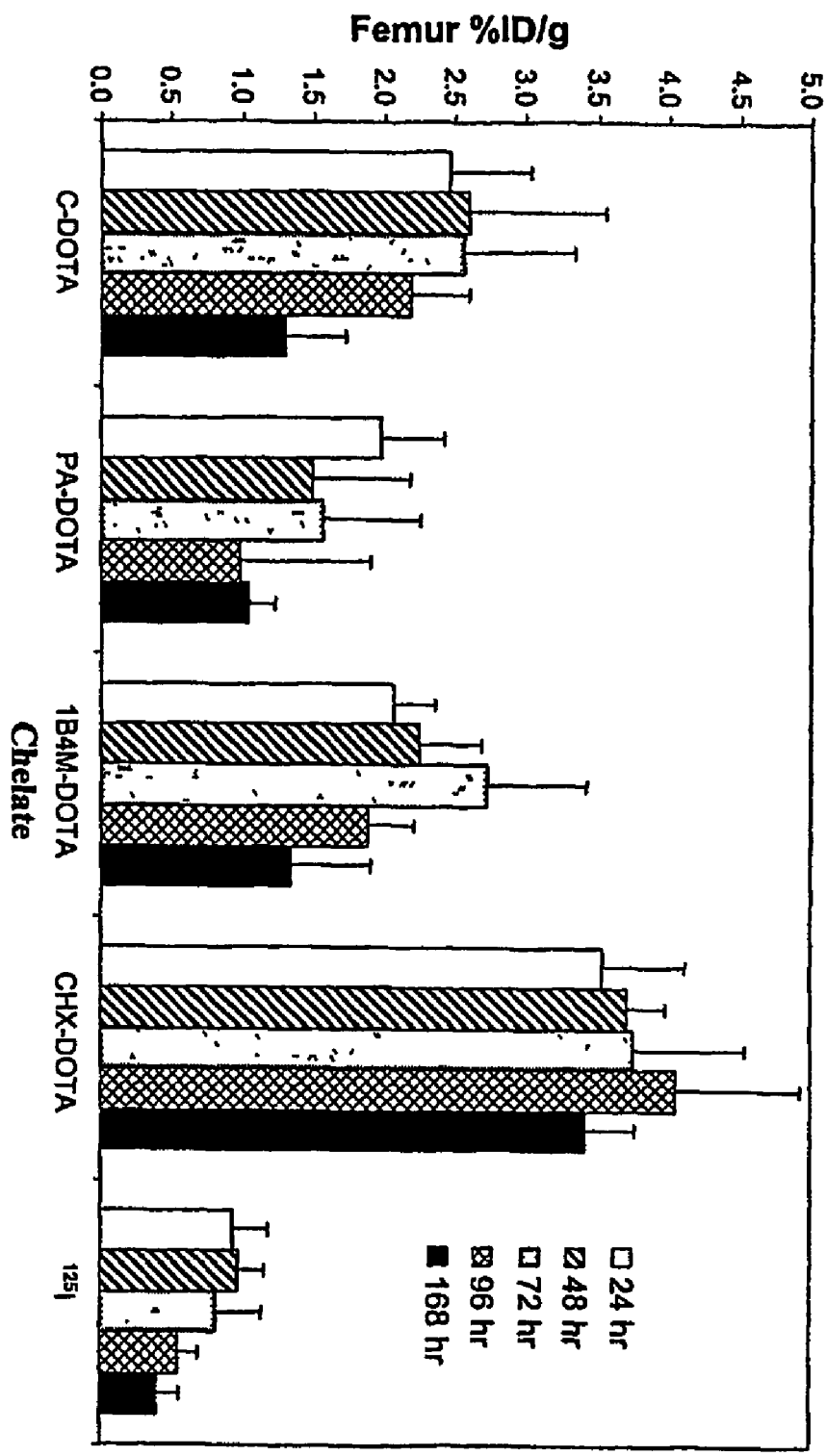
FIG. 6 is a bar graph illustrating the comparison of the uptake in bone of HERCEPTIN immunoconjugates radiolabeled with $^{177}$Lu.

Tissue-to-blood ratios were also calculated (Table 3 and FIG. 6) to gauge more accurately and compare the in vivo stability of each of the $^{177}$Lu-labeled immunoconjugates. If the radioactivity in the tissues is due to specific accumulation, then the tissue-to-blood ratio would increase as a function of time. If the radioactivity in the tissues is a result of that radioactivity present in the plasma compartment, then the tissue-to-blood ratio would remain constant with time. The femur-to-blood ratios were relatively constant for the C-DOTA and PA-DOTA conjugates. The 1B4M-DOTA (7) RIC yielded similar results up to the 168 h time point, at which time there was a slight increase over the 96 h time point (0.18 to 0.52). The femur-to-blood ratios for the CHX-DOTA (14) RIC were higher overall than the other RIC and also exhibited an increase from 0.60 at 96 h to 1.09 at 168 h.

TABLE 3

Comparison of the in vivo stability of Herceptin™ radiolabeled with $^{177}$Lu using bifunctional chelates: Tissue-to-Blood Ratios[a]

| Conjugate | Tissue | Time (h) | | | | |
|---|---|---|---|---|---|---|
| | | 24 | 48 | 72 | 96 | 168 |
| C-DOTA (comparative) | Liver | 0.38 | 0.68 | 0.52 | 0.44 | 1.02 |
| | Spleen | 0.35 | 0.47 | 0.47 | 0.41 | 0.78 |
| | Kidney | 0.30 | 0.39 | 0.47 | 0.33 | 0.50 |
| | Lung | 0.36 | 0.34 | 0.41 | 0.44 | 0.49 |
| | Femur | 0.14 | 0.20 | 0.22 | 0.19 | 0.23 |
| PA-DOTA (comparative) | Liver | 0.62 | 0.99 | 1.22 | 1.91 | 1.77 |
| | Spleen | 0.56 | 0.89 | 0.76 | 1.08 | 1.30 |
| | Kidney | 0.34 | 0.40 | 0.49 | 0.73 | 0.57 |
| | Lung | 0.40 | 0.38 | 0.43 | 0.48 | 0.47 |
| | Femur | 0.16 | 0.17 | 0.22 | 0.23 | 0.31 |
| 1B4M-DOTA (7) | Liver | 0.37 | 0.32 | 0.46 | 0.40 | 2.87 |
| | Spleen | 0.29 | 0.30 | 0.42 | 0.43 | 1.22 |
| | Kidney | 0.28 | 0.28 | 0.37 | 0.30 | 0.88 |
| | Lung | 0.40 | 0.36 | 0.45 | 0.41 | 0.70 |
| | Femur | 0.15 | 0.16 | 0.23 | 0.18 | 0.52 |
| CHX-DOTA (14) | Liver | 0.94 | 0.58 | 0.97 | 0.86 | 1.99 |
| | Spleen | 0.71 | 0.48 | 0.66 | 0.61 | 1.13 |
| | Kidney | 0.55 | 0.44 | 0.53 | 0.47 | 0.83 |
| | Lung | 0.51 | 0.37 | 0.51 | 0.46 | 0.79 |
| | Femur | 0.40 | 0.39 | 0.56 | 0.61 | 1.09 |
| $^{125}$I | Liver | 0.30 | 0.34 | 0.33 | 0.29 | 0.45 |
| | Spleen | 0.31 | 0.30 | 0.31 | 0.28 | 0.37 |
| | Kidney | 0.25 | 0.26 | 0.29 | 0.23 | 0.30 |
| | Lung | 0.44 | 0.37 | 0.43 | 0.44 | 0.48 |
| | Femur | 0.10 | 0.11 | 0.12 | 0.10 | 0.12 |

[a]Athymic mice bearing s.c. human colon carcinoma (LS-174T) xenografts were co-injected i.v. with approximately 2–5 µCi of $^{177}$Lu-labeled immunoconjugates and $^{125}$I-HERCEPTIN. The mice (n = 5) were sacrificed by exsanguinations as described above. The blood, tumor and major organs were collected and wet-weighed, and the radioactivity was measured. The tissue-to-blood ratios were calculated for each tissue.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of the formula (I), (II), or (III)

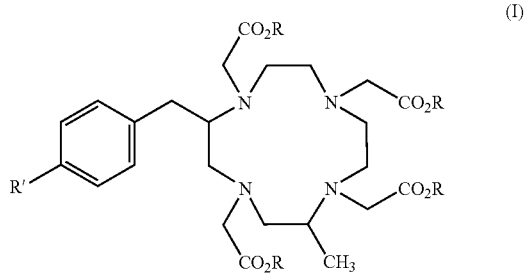

(I)

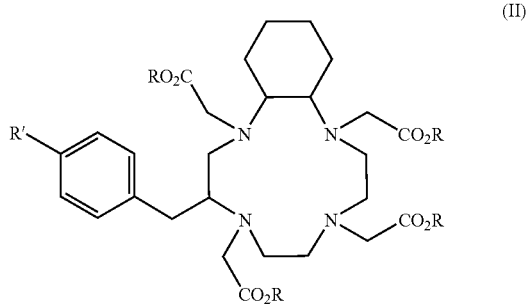

(II)

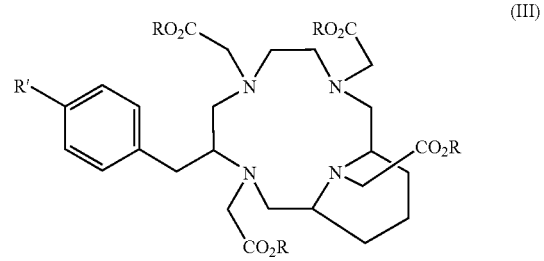

(III)

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido.

2. The compound of claim 1 of the formula

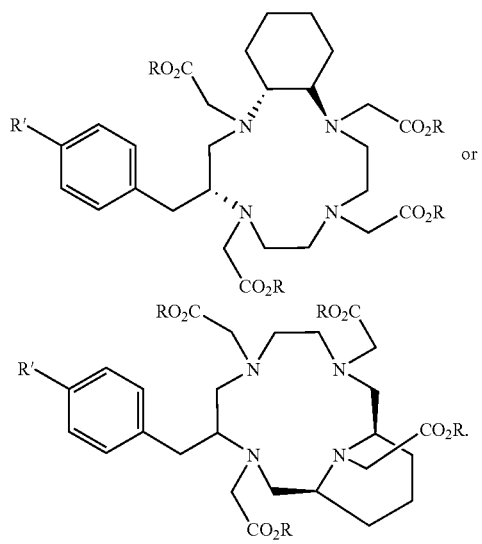

or

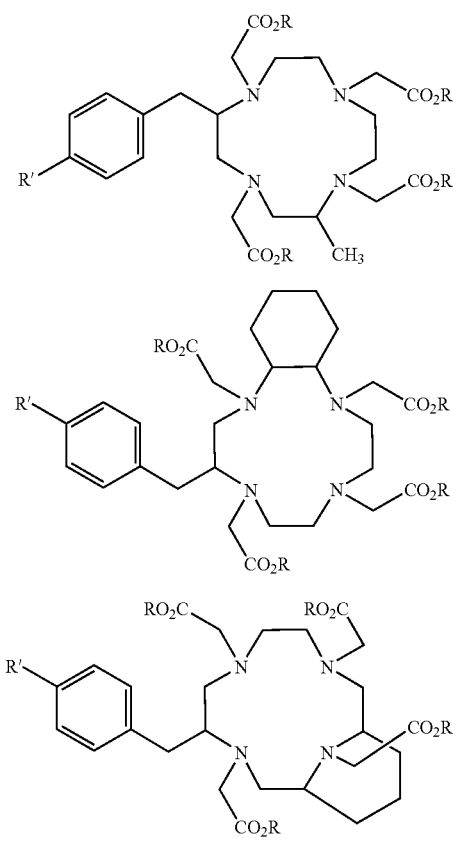

3. A complex comprising a compound of the formula (I), (II), or (III)

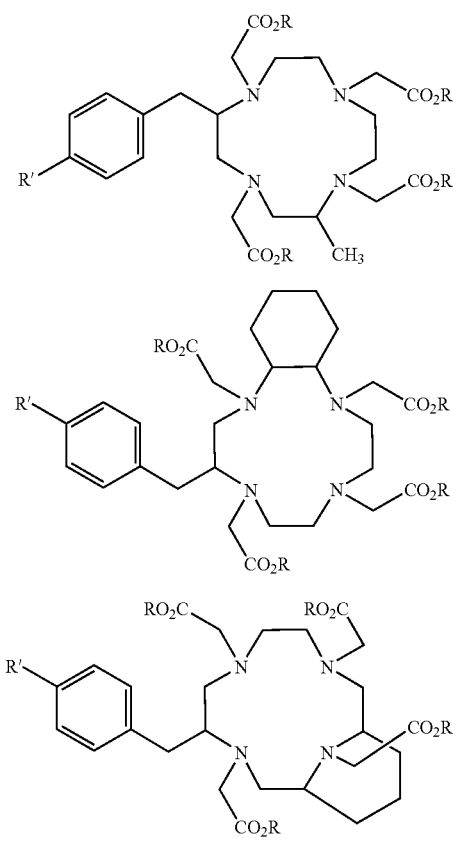

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido, and a metal ion, wherein the metal ion is optionally radioactive.

4. A complex comprising a compound of the formula

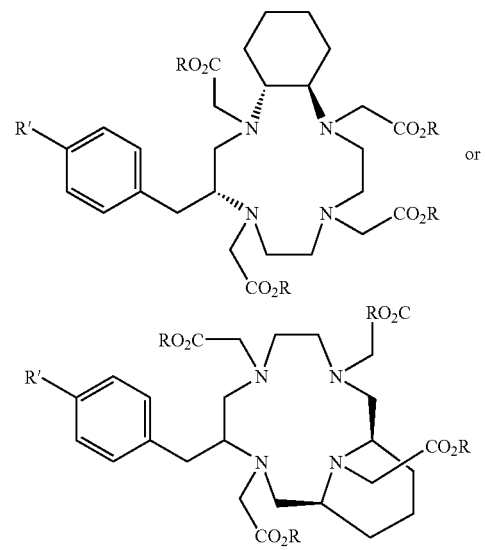

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, allylamido and haloalkylamido, and a metal ion, wherein the metal ion is optionally radioactive.

5. The complex of claim 3, wherein the metal ion is selected from the group consisting of ions of Bi, Pb, Y, Mn, Cr, Fe, Co, Ni, Tc, In, Ga, Cu, Re, Sm, a lanthanide, and an actinide.

6. The complex of claim 5, wherein the lanthanide ion is Gd(III).

7. A pharmaceutical composition comprising a pharmaceutically acceptable carrier and a compound of claim 1.

8. A pharmaceutical composition comprising a pharmaceutically acceptable carrier and a complex of claim 3.

9. A method for diagnostic imaging of a host, which method comprises:
(i) administering to the host a complex of claim 3 in an amount effective to provide an image; and
(ii) exposing the host to an energy source, whereupon a diagnostic image of the host is obtained.

10. A method for magnetic resonance imaging of a host, which method comprises:
(i) administering to the host a complex of claim 3 in which the metal ion is paramagnetic, in an amount effective to provide an image; and
(ii) exposing the host to a magnet, whereupon a magnetic resonance image of the host is obtained.

11. The method of claim 10, wherein the complex comprises Gd(III).

12. A method for x-ray imaging of a host, which method comprises:
   (i) administering to the host a complex of claim 3, in which the metal ion is radio-opaque, in an amount effective to provide an image; and
   (ii) exposing the host to x-rays, whereupon an x-ray contrast image of the host is obtained.

13. The method of claim 12, wherein the complex comprises an ion of $^{213}$Bi, $^{212}$Bi, $^{212}$Pb, $^{225}$Ac, $^{177}$Lu, $^{99m}$Tc, $^{111}$In, $^{11}$C, $^{13}$N, $^{123}$I, $^{186}$Re, $^{18}$F, $^{15}$O, $^{201}$Tl, $^{3}$He, $^{166}$Ho or $^{67}$Ga.

14. A method for single photon emission computed spectroscopy (SPECT) imaging, which method comprises:
   (i) administering to the host a complex of claim 3, in which the metal ion emits a single photon, in an amount effective to provide an image; and
   (ii) exposing the host to an energy source, whereupon a SPECT image of the host is obtained.

15. The method of claim 14, wherein the complex comprises an ion of $^{213}$Bi, $^{212}$Bi, $^{212}$Pb, $^{225}$Ac, $^{177}$Lu, $^{99m}$Tc, $^{111}$In, $^{11}$C, $^{13}$N, $^{123}$I, $^{186}$Re, $^{18}$F, $^{15}$O, $^{201}$Tl, $^{3}$He, $^{166}$Ho or $^{67}$Ga.

16. A conjugate comprising a complex and a biomolecule, wherein the complex comprises a compound of the formula (I), (II). or (III)

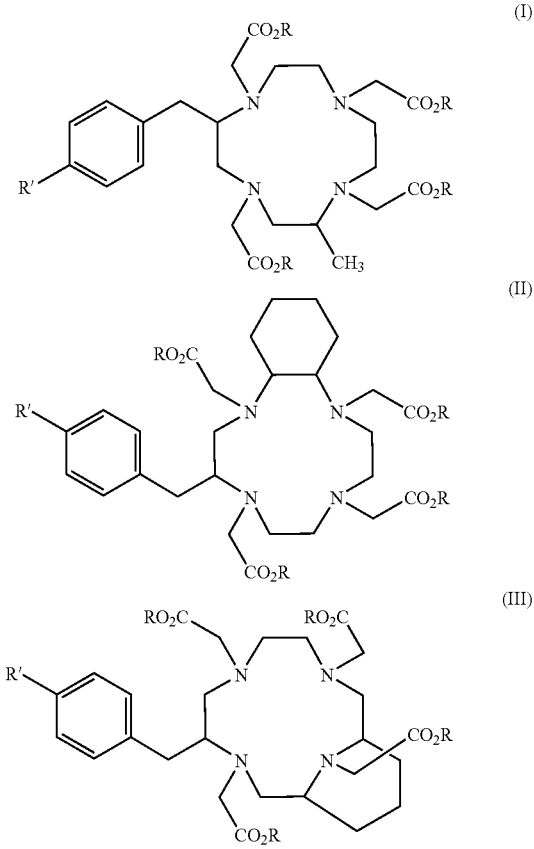

wherein R is hydrogen or alkyl and R' is selected from the group consisting of hydrogen, halo, alkyl, hydroxy, nitro, amino, alkylamino, thiocyano, isotbiocyano, carboxyl, carboxyalkyl, carboxyalkyloxy, amido, alkylamido and haloalkylamido, and
a metal ion, wherein the metal ion is optionally radioactive.

17. The conjugate of claim 16, wherein the biomolecule is selected from the group consisting of a hormone, an amino acid, a peptide, a peptidomimetic, a protein, deoxyribonucleic acid (DNA), ribonucleic acid (RNA), a lipid, an albumin, a polyclonal antibody, a receptor molecule, a receptor binding molecule, a hapten, a monoclonal antibody and an aptamer.

18. A pharmaceutical composition comprising a pharmaceutically acceptable carrier and a compound of claim 2.

19. A method for magnetic resonance imaging of a host, which method comprises:
   (i) administering to the host a complex of claim 4, in which the metal ion is paramagnetic, in an amount effective to provide an image; and
   (ii) exposing the host to a magnet, whereupon a magnetic resonance image of the host is obtained.

20. A method for x-ray imaging of a host, which method comprises:
   (i) administering to the host a complex of claim 4, in which the metal ion is radio-opaque, in an amount effective to provide an image; and
   (ii) exposing the host to x-rays, whereupon an x-ray contrast image of the host is obtained.

21. A method for single photon emission computed spectroscopy (SPECT) imaging, which method comprises:
   (i) administering to the host a complex of claim 4, in which the metal ion emits a single photon, in an amount effective to provide an image; and
   (ii) exposing the host to an energy source, whereupon a SPECT image of the host is obtained.

22. A conjugate comprising a complex and a biomolecule, wherein the complex comprises a compound of the formula

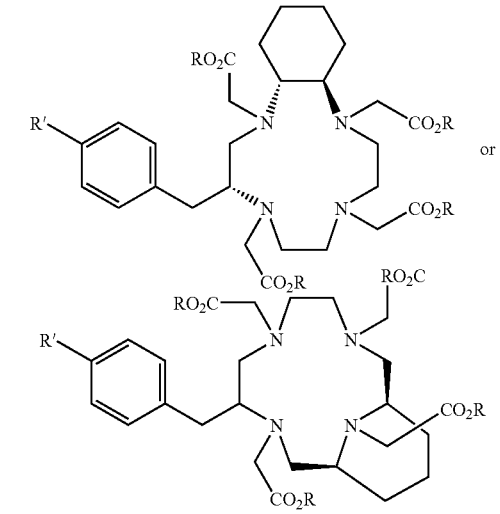

wherein R is hydrogen or alkyl and R' is selected from the group consisting of hydrogen, halo, alkyl, hydroxy, nitro, amino, alkylamino, thiocyano, isothiocyano, carboxyl, carboxyalkyl, carboxyalkyloxy, amido, alkylamido and haloalkylamido, and
a metal ion, wherein the metal ion is optionally radioactive.

* * * * *